United States Patent [19]
Bini et al.

[11] Patent Number: 6,043,087
[45] Date of Patent: Mar. 28, 2000

[54] MONOSPECIFIC ANTIBODY REACTIVE WITH MATRIX METALLOPROTEINASE CLEAVAGE PRODUCTS OF FIBRIN(OGEN)

[75] Inventors: Alessandra Bini, New York, N.Y.; Bohdan J. Kudryk, Hillsdale, N.J.

[73] Assignee: The New York Blood Center, New York, N.Y.

[21] Appl. No.: 08/900,895

[22] Filed: Jul. 25, 1997

[51] Int. Cl.$^7$ .............................. C12N 5/20; C07K 16/36; G01N 33/543; G01N 33/544
[52] U.S. Cl. ..................... 435/337; 435/7.24; 435/7.8; 435/7.92; 435/13; 435/70.21; 435/172.2; 436/518; 436/524; 436/528; 436/529; 436/530; 436/531; 436/534; 436/548; 530/387.3; 530/387.9; 530/388.25; 530/389.3; 530/391.1; 530/391.3; 935/15; 935/104
[58] Field of Search ..................................... 435/7.1, 7.24, 435/7.8, 7.92, 7.93, 7.94, 7.95, 13, 23, 70.21, 172.2, 240.27, 69.6, 337, 331; 436/516, 518, 525, 528, 529, 530, 534, 538, 548, 69, 531; 935/15, 100, 104, 106, 107, 108; 530/387.3, 387.9, 388.25, 389.3, 391.1, 391.3; 424/133.1, 139.1, 145.1

[56] References Cited

FOREIGN PATENT DOCUMENTS 0 345 811 B1  12/1989  European Pat. Off. .

OTHER PUBLICATIONS

Bini et al., 1995. Degradation of fibrinogen and lysis of fibrin clots by matrix metalloproteinase 3. Circulation 92 (8 Suppl.): 1–623 Abstract #2986.

Bini et al., 1996a Degradation of cross–linked fibrin by matrix metalloproteinase 3 (stromelysin 1): hydrolysis of γGly 404–Ala 405 peptide bond. FASEB J. 10(6): A1016, Abstract #97.

Campbell, 1991. *Monoclonal Antibody and Immunosensor Technology*, Elsevier, Amsterdam. pp. 3–6, 20–23, 42–45.

Chung et al., 1983. Characterization of complementary deoxyribonucleic acid and genomic deoxyribonucleic acid for the β chair of human fibrinogen. Biochemistry 22: 3244–3250.

Harlow et al., 1988. *Antibodies. A Laboratory Manual*, Cold Spring Harbor Laboratory, Cold Spring Harbor. pp. 72–77, 600–612.

Owens et al., 1994. The genetic engineering of monoclonal antibodies. J. Immunological Methods 168: 149–165.

Bini A, Callender S, Procyk R, Blombáck B and Kudryk BJ, "Flow and antibody binding properties of hydrated fibrins prepared from plasma, platelet rich plasma and whole blood," *Thrombosis Res* 76(2):145–156 (1994).

Bini A, Fenoglio JJ Jr, Mesa–Tejada R, Kudryk B and Kaplan KL, "Identification and distribution of fibrinogen, fibrin, and fibrin (ogen) degradation products in atherosclerosis," *Arteriosclerosis* 9(1):111–121 (1989).

Bini A, Fenoglio JJ, Sobel J, Owen J, Fejgl M and Kaplan KL, "Immunochemical characterization of fibrinogen, fibrin I and fibrin II in human thrombi and atherosclerotic lesions," *Blood* 69(4):1038–1045 (1987).

Bini A, Itoh Y, Kudryk BJ and Nagase H, "Degradation of cross–linked fibrin by matrix metalloproteinase 3 (stromelysin 1): Hydrolysis of γGly404–Ala405 peptide bond," *Biochemistry* 35(40):13056–13063 (1996).

Bini A and Kudryk BJ, "Fibrin and its derivatives in the normal and diseased vessel wall," *Ann NY Acad Sci* 667:112–126.

Bini A, Mesa–Tejada R, Fenoglio JJ Jr, Kudryk B and Kaplan KL, "Immunohistochemical characterization of fibrin(ogen)–related antigens in human tissues using monoclonal antibodies," *Laboratory Investigation* 60(6):814–821 (1989).

Collen D and Lijnen HR, "Basic and clincal aspects of fibrinolysis and thrombolysis," *Blood* 78(12):3114–3124 (1991).

Fu Y and Grieninger G, "Fib$_{420}$: A normal human variant of fibrinogen with two extended α chains," *Proc Natl Acad Sci USA* 91:2625–2628 (1994).

Fu Y, Weissbach L, Plant PW, Oddoux C, Cao Y, Liang TJ, Roy SN, Redman CM and Grieninger G, "Carboxy–Termina–Extended variant of the human fibrinogen α subunit: a novel exon conferring marked homology to β and γ subunits," *American Chemical Society* 31(48):11968–11972.

Koopman J, Haverkate F, Grimbergen J, Egbring R and Lord ST, "Fibrinogen Marburg: A homozygous case of dysfibrinogenemia, lacking amino acids Aα 461–610 (Lys 461 AAA → Stop TAA)," *Blood* 80(8):1972–1979 (1992).

Kudryk B, Bini A, Procyk R, Matsueda GR and Shainoff JR, "Cross–linking of fibrinogen by tissue transglutaminase: Involvement of the C–termini of the Aα– and γ–chains in formation of Aαγ–dyads," *Thromb Haemostas* 69(6):1260 (1993).

Kudryk, B, Gidlund M, Rohoza A, Ahadi M, Coiffe D and Weitz JI, "Use of a synthetic homologue of human firbinopeptide A for production of a monoclonal antibody specific for the free peptide," *Blood* 74(3):1036–1044 (1989).

Kudryk BJ, Grossman ZD, McAfee JG and Rosebrough SF, "Monoclonal antibodies as probes for fibrin(ogen) proteolysis," *Monoclonal Antibodies in Immunoscrinitgraphy* J–F. Chatal, ed. CRC Press, Boca Raton 365–398 (1989a).

(List continued on next page.)

*Primary Examiner*—Christopher L. Chin
*Assistant Examiner*—James L. Grun
*Attorney, Agent, or Firm*—Hoffmann & Baron, LLP

[57] ABSTRACT

The invention provides a monospecific antibody that is specifically reactive with enzymatically mediated degradation products of fibrin(ogen) (i.e., fibrin, fibrinogen, and related substances). The monospecific antibody of the invention is specifically reactive with an epitope defined by an amino acid sequence SEQ ID NO:1. The invention further provides compositions containing a monospecific antibody, optionally detectably labeled, for the performance of fibrinolytic or thrombolytic analyses. The invention further provides continuous cell lines (hybridomas) that produce monospecific antibodies as described.

13 Claims, 15 Drawing Sheets

OTHER PUBLICATIONS

Kudryk B, Robinson D, Netre C, Hessel B, Blombáck M, and Blombáck B, "Measurement in human blood of fibrinogen/fibrin fragments containing the Bβ15–42 sequence," *Thromb Res* 25:277–291 (1982).

Kudryk B, Rohoza A, Ahadi M, Chin J and Wiebe ME, "A monoclonal antibody with ability to distinguish between NH$_2$–terminal fragments derived from fibrinogen and fibrin," *Mol Immunol* 20:1191–1200 (1983).

Kudryk B, Rohoza A, Adhadi M, Chin J, and Wiebe ME, "Specificity of a monoclonal antibody for the NH$_2$–terminal region of fibrin," *Mol Immunol* 21:89–94 (1984).

Kudryk B, Rohoza A, Ahadi M, Gidlund M, Procyk R and Matsueda GR, *Thromb Haemostas* 65:898 (Abstract 714) (1991).

Liu CY, Sobel JH, Weitz JI, Kaplan KL, and Nossel HL, "Immunologic identification of the cleavage products for the A alpha– and B beta–chains in the early stages of plasmin digestion of fibrinogen," *Thromb Haemostas* 56(1):100–106 (1986).

Loike JD, Sodeik B, Cao L, Leucona S, Weitz JI, Detmers PA, Wright SD and Silverstein SC, "CD11c/CD18 on neutrophils recognizes a domain at the N terminus of the A–alpha chain of fibrinogen," *Proc Natl Acad Sci USA* 88:1044–1048 (1991).

Plow EF and Edgington TS, "Surface markers of fibrinogen and its physiologic derivatives revealed by antibody probes," *Semin Thromb Haemostas* 8(1):36–56 (1982).

Procyk R, Kudryk B, Callender S, Blombáck B, "Accessibilty of epitopes on fibrin clots and fibrinogen gels," *Blood* 77:1469–1475 (1991).

Singer II, Kawka DW, Bayne EK, Donatelli SA, Weidner JR, Williams HR, Ayala JM, Mumford RA, Lark MW, Glant TT, Nabozny GH and David CS, "VDIPEN, A metalloproteinase–generated neoepitope, is induced and immunolocalized in articular cartilage during inflammatory arthritis," *J Clinical Investigation, Inc.* 95:2178–2186 (1995).

Valenzuela R, Shainoff JR, DiBello PM, Urbanic DA, Anderson JM, Matsueda GR and Kudryk BJ, "Immunoelectrophoretic and immunohistochemical characterizations of fibrinogen derivatives in atherosclerotic aortic intimas and vascular prosthesis pseudo–intimas," *Amer J Pathol* 141(4):861–880 (1992).

Weissbach L and Grieninger G, "Bipartite mRNA for chicken α–fibrinogen potentially encodes an amino acid sequence homologous to β– and γ–fibrinogens," *Proc Natl Acad Sci USA* 87:5198–5202 (1990).

PROTEIN STAINED GEL

IMMUNOBLOT
(T54-2)

IMMUNOBLOT
(P10)

PROTEIN STAIN

IMMUNOBLOT
(T54-2)

IMMUNOBLOT
(T15-1)

PROTEIN STAIN

IMMUNOBLOT
(T54-2)

IMMUNOBLOT
(T15-1)

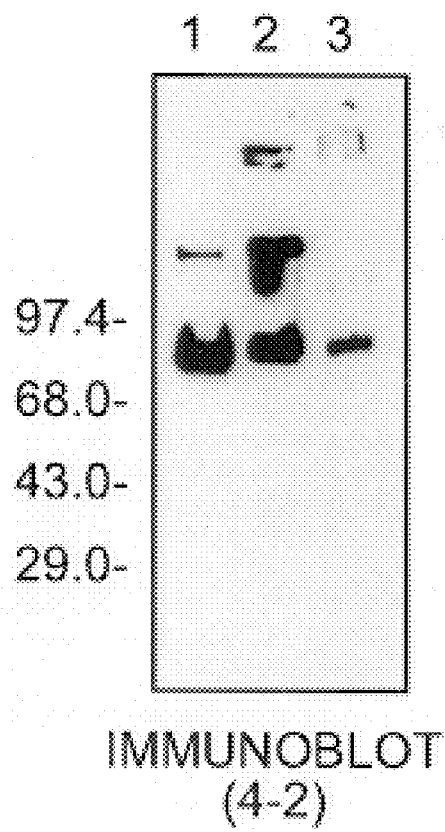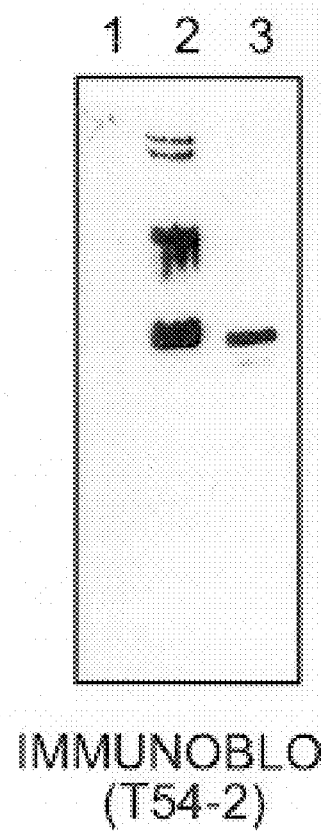

IMMUNOBLOT
(T54-2)

IMMUNOBLOT
(Ea3)

IMMUNOBLOT
(T54-2)

IMMUNOBLOT
(Ea3)

IMMUNOBLOT
(T54-2)

IMMUNOBLOT
(Ea3)

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:1:

Asp Leu Trp Gln Lys
1                5

(2) INFORMATION FOR SEQ ID NO:2:

(i) SEQUENCE CHARACTERISTICS:
      (A) LENGTH: 6 amino acids
      (B) TYPE: amino acid
      (D) TOPOLOGY: linear (ii) MOLECULE TYPE: peptide (xi) SEQUENCE DESCRIPTION: SEQ ID NO:2:

Asp Leu Trp Gln Lys Arg
1                5

MONOSPECIFIC ANTIBODY REACTIVE WITH MATRIX METALLOPROTEINASE CLEAVAGE PRODUCTS OF FIBRIN(OGEN)

BACKGROUND OF THE INVENTION

This invention relates to a probes and methods of detecting and measuring enzyme-mediated breakdown of fibrinogen and fibrin. More particularly, the invention relates to a probe and a method for detecting degradation of fibrinogen and related substances mediated by fibrin(ogen)olytic matrix metalloproteinases.

The clotting of blood is part of the body's natural response to injury or trauma. Blood clot formation derives from a series of events called the coagulation cascade, in which the final steps involve the formation of the enzyme thrombin. Thrombin converts circulating fibrinogen into fibrin, a mesh-like structure which forms the insoluble framework of the blood clot. As a part of hemostasis, clot formation is often a life-saving process in response to trauma and serves to arrest the flow of blood from severed vasculature.

The normally beneficial process of clot production in response to an injury can become life-threatening when it occurs at inappropriate places in the body. For example, a clot can obstruct a blood vessel and stop the supply of blood to an organ or other body part. In addition, the deposition of fibrin contributes to partial or complete stenosis of blood vessels, resulting in chronic diminution of blood flow. Equally life-threatening are clots that become detached from their original sites and flow through the circulatory system causing blockages at remote sites. Such clots are known as embolisms. Indeed, pathologies of blood coagulation, such as heart attacks, strokes, and the like, have been estimated to account for approximately fifty percent of all hospital deaths.

Fibrinogen is one of the more well-studied and abundant proteins in the human circulatory system. By the late 1960s, the general subunit structure of fibrinogen was firmly established (Blombäck 1968) and, a decade later, the complete amino acid sequence was reported (Lottspeich et al. 1977; Henschen et al. 1977; Henschen et al. 1979; Doolittle et al. 1979). Over the next 10 years, the cluster of three separate genes encoding the α (alpha), β (beta), and γ (gamma) subunits was identified on chromosome 4q23-q32 (Kant et al. 1985), and the apparently complete genetic sequences of all three fibrinogen subunits were published (Chung et al. 1991).

Fibrinogen (also abbreviated herein as "Fg") is a heavily disulfide-bonded homodimeric protein, composed of two symmetrical units (monomers), each including single copies each or three polypeptide chains: the Aα (alpha), Bβ (beta), and γ (gamma) chains. Thus, fibrinogen has the generic structure $(A\alpha B\beta\gamma)_2$. For a review see Doolittle (1987). All three of the fibrinogen subunits have coiled domains, which permit the subunits to engage one another to form a "coiled coil" region in the fibrinogen monomer. In addition, the Bβ and γ chains each have a globular domain, while the Aα chain is present in two forms; a predominant form having no corresponding globular domain (Aα), and a less prevalent form in which a globular domain is present $(A\alpha_E)$ (Fu et al. 1992; 1994). Accordingly, because fibrinogen is homodimeric and because two forms of the Aα subunit have been identified, two principal forms of fibrinogen are recognized: $(A\alpha B\beta\gamma)_2$ and $(A\alpha_E B\beta\gamma)_2$.

Fibrinogen's complex structure, and its central role in blood clot formation and wound healing account for the high profile it has enjoyed as a subject of both biochemical and medical research. Recently, new attention has been given to structure/function relationships in the fibrinogen molecule. This new interest has in part been prompted by growth in the understanding of this protein's range of activity in normal and pathological states (Blombäck 1991; Bini et al. 1992; Dvorak 1992). Moreover, antibodies have been developed which are specifically reactive with or specifically bind to only some of the fragments, thereby permitting molecular identification of certain fragments with great accuracy and precision (Kudryk et al. 1989a). However, despite these advances, the complexity of fibrinogen and its metabolic system have to date eluded complete elucidation.

Fibrinogen is synthesized and secreted into the circulation by the liver. Circulating fibrinogen is polymerized under attack by thrombin to form fibrin, which is the major component of blood clots or thrombi. Subsequently, fibrin is depolymerized under attack by plasmin to restore the fluidity of the plasma. Many of the steps in the polymerization and depolymerization processes have been well established (Doolittle 1984). The elevated levels of fibrinogen which are part of the acute phase response occurring in the wake of infections and trauma are now known to come from increased hepatic production, primarily in response to interleukin-6 (IL-6) (Sehgal et al. 1989).

In wound repair, fibrinogen serves as a key protein, achieving rapid arrest of bleeding following vessel injury. It promotes both the aggregation of activated platelets with one another to form a hemostatic plug, as well as endothelial cell binding at the site of injury to seal the margins of the wound. As the most abundant adhesive protein in the blood, fibrinogen attaches specifically to platelets, endothelial cells and neutrophils via different integrins (Hynes 1992). Five putative receptor recognition domains on human fibrinogen, distributed over its three subunits, have been identified by in vitro and in vivo analyses (Kloczewiak et al. 1984; Cheresh et al. 1989; Loike et al. 1991; Farrell et al. 1992; Gonda et al. 1982; Ribes et al. 1989).

Elevated levels of fibrinogen have been found in patients suffering from clinically overt coronary heart disease, stroke and peripheral vascular disease. Although the underlying mechanisms remain speculative, recent epidemiological studies leave little doubt that plasma fibrinogen levels are an independent cardiovascular risk factor possessing predictive power which is at least as high as that of other accepted risk factors such as smoking, hypertension, hyperlipoproteinemia or diabetes (Ernst 1990; Ernst et al. 1993). The structure of fibrin has been analyzed extensively in vitro (Doolittle 1984). Only recently, however, has attention been paid to the molecular structure of human thrombi and atherosclerotic plaques with respect to fibrinogen and fibrin products (Bini et al. 1987). Whereas thrombi formed in vivo consist primarily of fibrin II cross-linked by factor XIIIa, fibrinogen itself is a major component of uncomplicated atherosclerotic lesions, particularly fibrous and fatty plaques. Immunohistochemical as well as immunoelectrophoretic analyses indicate that fibrinogen in the aortic intima is comparatively well protected from thrombin and plasmin, and that much of it is deposited through direct cross-linking by tissue transglutaminase without becoming converted to fibrin (Valenzuela et al. 1992). Further understanding of these issues awaits the development of methods for the differential determination of fibrinogen subtypes in medical samples.

Fibrinogen-derived protein is also a major component of the stroma in which tumor cells are embedded, but little is known about its molecular structure. Tumor cells promote the secretion of potent permeability factors which cause leakage of fibrinogen from blood vessels (Dvorak et al.

1992). Extravascular clotting occurs due to procoagulants associated with tumor cells. The resulting fibrinogen/fibrin matrix is constantly remodeled during tumor growth as a consequence of fibrinolysis induced by tumor cell-derived plasminogen activators. It is assumed that fibrin/fibrinogen degradation products play a role during escape of metastatic tumor cells from the primary tumor. There are indications that integrin $\alpha_v\beta_3$, which is known to interact with the RGDS site in the C-terminal region of the $\alpha$ chain, may be an important tumor cell surface receptor since it is preferentially expressed on invasive melanoma (Felding-Habermann et al. 1992).

The formation of fibrin during inflammation, tissue repair, or hemostasis, plays only a temporary role and must be removed when normal tissue structure and function is restored. Thus, a fibrin clot that forms quickly to stop hemorrhage in an injured blood vessel is remodeled and then removed to restore normal blood flow as healing occurs. The system responsible for fibrin breakdown and clot removal is the fibrinolytic system. Action of the fibrinolytic system is tightly coordinated through the interaction of activators, zymogens, enzymes, as well as through inhibitors of each of these components, to provide focused local activation at sites of fibrin deposition (Francis et al. 1994; Collen 1980; Collen et al. 1991).

The principal mediator of fibrinolysis is plasmin, a trypsin-like endopeptidase which cleaves fibrin to dissolve clots and to permit injured tissues to regenerate. Plasmin has also been demonstrated to play a role in degrading proteins involved in cell-cell and cell-matrix interactions, as well as in activating other tissue remodeling enzymes such as matrix metalloproteinases (Murphy et al. 1992). In turn, control of plasmin activity, as well as these other extracellular events, is principally mediated by plasminogen activators, which convert the inactive zymogen plasminogen to the active enzyme plasmin.

Enzymes other than plasmin are also known which can degrade fibrin(ogen) to different extents. For example, endogenous leukocyte proteases (Bilezikian et al. 1977; Plow et al. 1975), later identified as elastase and cathepsin-G (Gramse et al. 1978; Plow 1980; Plow et al. 1982), can partially degrade fibrin(ogen). Exogenous enzymes are also known which degrade fibrin. Such enzymes include hemolytic enzymes collected from the venom of certain snakes, e.g., the families crotalidae and viperidae (Purves et al. 1987; Retzios et al. 1992; Sanchez et al. 1991). Fibrinolytic enzymes isolated from snakes can be grouped into two different classes (Guan et al. 1991). Those enzymes that preferentially degrade the A$\alpha$-chain of fibrinogen and also the $\alpha$- and $\beta$-chains of fibrin are zinc metalloproteases (Guan et al. 1991) and all can be inhibited by EDTA. Enzymes in the second class are serine proteinases, and exhibit specificity for the $\beta$-chain of fibrin (Guan et al. 1991). An endopeptidase from puff adder venom (*Bitis arietans*) can cleave at the $\gamma$-chain cross-linking site and thereby cleave Fragment D-dimer into a D-like monomer (Purves et al. 1987). Fibrinolytic enzymes have also been obtained from leeches (Zavalova et al. 1993; Budzynski 1991), as well as from the growth medium of a bacterium (*Aeromonas hydrophila*) which was recovered from leech intestinal tract (Loewy et al. 1993).

Endogenous matrix metalloproteinases (MMPs) or "matrixins" include three classes of enzymes: collagenases, gelatinases, and stromelysins. MMPs are known to have the capacity to degrade a number of proteins and proteoglycans which are associated with the extracellular matrix (ECM) of connective tissue. They have been shown to break down a number of proteins including collagen (Types I–IV, VII and X), laminin, fibronectin, elastin and proteoglycans. MMPs have also been identified in leukocytes (Welgus et al. 1990). It has been shown that MMP-2 and MMP-9 possess elastase activity (Senior et al. 1991), to which some of the complex proteolytic activity, initially observed in granulocytes, could be attributed (Sterrenberg et al. 1983). MMPs participate in the remodeling of tissues in physiological processes such as morphogenesis and embryonic development, as well as in the pathophysiology of wound healing, tumor invasion, and arthritis (Matrisian 1992; Nagase et al. 1991; Woessner 1991; Werb et al. 1992).

From the foregoing discussion, it becomes clear that significant gaps exist in the understanding of processes involved in thrombus formation and degradation. While certain approaches have been identified which permit a measure of control over these processes, these approaches suffer serious deficiencies related to cost, efficacy, or safety. The diagnosis and treatment of disease states associated with physiological processes involving fibrinogen and fibrin have also been found lacking.

As a result, there exists a need for effective compositions and methods for use in illuminating the processes underlying thrombus development and thrombolysis, and for assessing these processes in vivo as they manifest as clot formation, embolism, atherosclerosis and the treatment of these processes In addition, there exists a need for diagnostic and experimental materials and methods for revealing more information concerning the physical and chemical processes involved in thrombus formation and degradation.

SUMMARY OF THE INVENTION

The present invention provides a monospecific antibody, that binds with an epitope defined by an amino acid sequence SEQ ID NO:1. In particular, the antibody is specifically reactive with enzymatically cleaved fragments of fibrin and fibrinogen (i.e., fibrin(ogen)) that contain SEQ ID NO:1. In non-digested fibrin(ogen), this sequence is unavailable to react with the monospecific antibody of the invention.

Preferably the monospecific antibody is detectably labeled by conjugation to a detectable moiety. The detectable moiety can be selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

The monospecific antibody may be attached to a substrate. Suitable substrates can include a component selected from the group consisting of gels, hydrogels, resins, beads, nitrocellulose, nylon filters, microtiter plates, culture flasks, and polymeric materials.

The monospecific antibody of the invention may comprise an antigen-binding region, which may be selected from the group consisting of Fab, F(ab')$_2$, and Fv fragments.

The monospecific antibody may be a modified, synthetic, recombinant, or chimeric antibody. Preferably, the monospecific antibody is a monoclonal antibody. More preferably, the antibody is a monoclonal antibody produced by the hybridoma cell line identified as T54-2.

Preferably, the antibody binds with matrix metalloproteinase-mediated cleavage fragments of fibrin (ogen) comprising an epitope characterized by an amino acid sequence defined by SEQ ID NO:1. More preferably, the cleavage fragments are mediated by cleavage with MMP-3 or MMP-7.

The invention also provides a composition for selectively binding a matrix metalloproteinase-mediated cleavage fragment of fibrin(ogen), comprising a monospecific antibody that binds specifically with an epitope defined by an amino acid sequence SEQ ID NO:1.

Preferably, the composition includes a monospecific antibody which is detectably labeled by conjugation to a detectable moiety. Again, the detectable moiety for labeling the antibody can be is selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

Alternatively, the composition may include an antibody attached to a substrate. Suitable substrate can include a component selected from the group consisting of gels, hydrogels, resins, beads, nitrocellulose, nylon filters, microtiter plates, culture flasks, and polymeric materials.

The monospecific antibody in the composition may comprise an antigen-binding region, and the antigen-binding region may selected from the group consisting of Fab, F(ab')$_2$, and Fv fragments. The antibody may be a modified, synthetic, recombinant, or chimeric antibody. Preferably, the antibody in the composition is a monoclonal antibody. More preferably, the antibody is a monoclonal antibody produced by the hybridoma cell line identified as T54-2.

The composition may further comprise a differentiating component that binds specifically with another domain of fibrin(ogen) or a fragment thereof. Preferably, the differentiating component is an second antibody, that binds specifically with another domain of fibrin(ogen) or a fragment thereof.

The invention also provides a method of detecting fibrin (ogen) or a matrix metalloproteinase-mediated cleavage fragment thereof, the method comprising:
    contacting a testable system with a composition comprising a monospecific antibody that binds specifically with an epitope defined by an amino acid sequence SEQ ID NO:1, and
    measuring specific binding of the antibody in the testable system; wherein specific binding of the antibody in the testable system is associated with the presence of fibrin(ogen) in the sample.

Accordingly, the method may be selected from the group consisting of enzyme-linked immunosorbent assay methods, immunonephelometry methods, agglutination methods, precipitation methods, immunodiffusion methods, immunoelectrophoresis methods, immunofluorescence methods, radioimmunoassay methods, and immunohistochemistry methods.

In the method, the monospecific antibody may be detectably labeled by conjugation to a detectable moiety as described above. Alternatively, the antibody may be attached to a substrate, as described above.

The monospecific antibody useful according to the method may comprise an antigen-binding region, such as an antigen-binding region selected from the group consisting of Fab, F(ab')$_2$, and Fv fragments. The method can also employ an antibody which is a modified, synthetic, recombinant, or chimeric antibody. Preferably, the antibody is a monoclonal antibody, more preferably, a monoclonal antibody produced by the hybridoma cell line identified as T54-2.

Moreover, the invention provides a kit for the detection of fibrin(ogen) or a matrix metalloproteinase-mediated cleavage fragment thereof, comprising:
    (a) a composition comprising a monospecific antibody that binds specifically with an epitope defined by an amino acid sequence SEQ ID NO:1; and
    (b) a container housing the composition.

In the kit, the monospecific antibody is detectably labeled by conjugation to a detectable moiety, as described. Alternatively, the antibody can be attached to a substrate.

It is preferred that the antibody in the kit is a monoclonal antibody, more preferably a monoclonal antibody produced by the hybridoma cell line identified as T54-2.

The invention further provides a diagnostic method for characterizing fibrin(ogen), comprising:
    contacting fibrin(ogen) with a fibrinolytic matrix metalloproteinase to provide characteristic matrix metalloproteinase-mediated degradation products of the fibrin(ogen);
    contacting the degradation products with at least one monospecific antibody that binds specifically with an epitope defined by an amino acid sequence SEQ ID NO:1, and
    measuring specific binding of the antibody to the degradation products.

The method is especially useful in characterizing fragments of fibrin(ogen) that are cleaved by MMP-3 or MMP-7.

The method can employ the antibody detectably labeled with a detectable marker moiety, or an antibody that is bound to a substrate. Preferably, the antibody is a monospecific antibody, more preferably a monoclonal antibody consisting of the monoclonal antibody produced by the hybridoma cell line identified as T54-2.

Also, the invention provides a continuous cell line, that produces a monoclonal antibody that binds specifically with fragments of fibrin(ogen) that contain an epitope characterized by the amino acid sequence defined by SEQ ID NO:1. A highly preferred continuous cell line is a hybridoma cell line identified as T54-2.

As a result of the invention, the artisan is now enabled to specifically detect important cleavage products of fibrin and fibrinogen, which permits the accurate and precise determination of thrombotic activity in individuals. Methods are provided for detecting such cleavage products by means of a monospecific antibody, and a variety of related immunological applications permit determination of the presence of the products in biological samples of many types. Thus, the artisan's ability to diagnose and treat thrombolytic disorders is significantly advanced.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 9A is an immunoblot of separated proteins using the 4-2 antibody as a probe; FIG. 9B is an immunoblot of separated proteins using the T54-2 antibody as a probe.

DETAILED DESCRIPTION OF THE INVENTION

Figure 1A:
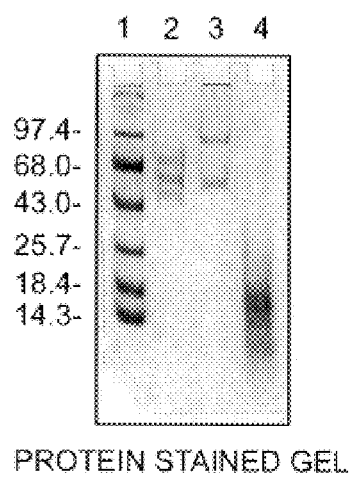
FIG. 1A is an electrophoretic separation of proteins, stained for protein.

Matrix metalloproteinases (MMPs) have the capacity to degrade a number of proteins and proteoglycans that constitute the extracellular matrix of connective tissue. These enzymes participate in the remodeling of tissues in physiological processes such as morphogenesis and embryonic development, and in the pathophysiology of wound healing, inflammation, tumor invasion, stroke, myocardial infarction, atherosclerosis and arthritis. The presence of fibrin(ogen)-related antigen (FRA) in vascular and extravascular space has been described in all of these disease states and we have hypothesized that lysis of FRA by MMPs may be relevant in some or all of these pathophysiological processes.

Our recent results, described in Bini et al. (1996), showed that both fibrinogen (Fg) and Factor XIIIa cross-linked fibrin (XL-Fb) can be substrates for MMPs with some differences among the various classes. MMP-1, a collagenase, seems to have little effect on both Fg and XL-Fb. MMP-2, a gelatinase, degrades fibrinogen rapidly and extensively. However, Fg degraded with MMP-2 still retains the ability to form a fibrin clot. On the contrary, Fg degraded with MMP-3 was unclottable, similarly to Fg previously degraded with plasmin. Of the three, MMP-3 was the only enzyme that was capable of dissolving a XL-Fb clot, similar to plasmin. More recently, we have also shown that MMP-7 (Matrilysin, MAT or PUMP-1) has a strong proteolytic action on Fg and has also the ability of solubilizing XL-Fb clots. However, its mechanism of action appears different from MMP-3. MMP-7 seems to generate fibrin(ogen) degradation products with a pattern similar to that obtained with plasmin. Additional details concerning the degradation of fibrin(ogen) by matrix metalloproteinases are found in U.S. application Ser. No. 08/859,738, the entire disclosure of which is incorporated herein by reference.

In our studies on the degradation of fibrin(ogen) by MMP-3 we have shown by sequence analysis that the cleavage sites for this enzyme are different from those split by plasmin. Additionally, we have also been able to distinguish MMP-3 and plasmin degradation products of fibrin (ogen) using specific monoclonal antibodies.

As described by Bini et al. (1996), digestion of Fg or XL-Fb by MMP-3 results in loss of reactivity with MoAb/ 4A5 (anti-γ 397-411). This is in contrast to plasmin where loss of this epitope from either substrate occurs only if digests with plasmin are carried out in a $Ca^{2+}$-free environment. In more recent studies, we have shown several other major immunochemical differences in MMP-3 vs. plasmin-generated digest products. Antibody 1D4 is directed to an epitope located in the carboxy-terminal region of the Aα-chain and reacts completely with intact fibrinogen, plasmin digests of Fg and XL-Fb, purified Aα-chain as well as the intact or trypsin-digested CNBr fragment of fibrinogen Aα-chain called Hi2-DSK (Aα241-476). Furthermore, this antibody shows similar reactivity with tryptic peptide Aα 349-406 and synthetic peptide Aα 392-402. By immunoblot and competition immunoassay, we have now shown that MMP-3 digests of Fg or XL-Fb result in near complete loss of the epitope reactive with antibody 1D4.

As noted, fibrin (also abbreviated herein as "Fb" or "XL-Fb" when cross-linked by Factor XIIIa) is generated through an induced and controlled polymerization of fibrinogen (Fu et al. 1994). Given that various forms of fibrinogen are found in circulating blood, it is known that various polymerization structures for fibrin occur. Fibrin structure can affect the processes of fibrinolysis (Gabriel et al. 1992). A fibrinolytic metalloproteinase has now been found to effectively lyse fibrin. It appears, therefore, that fibrinolytic metalloproteinases are active against fibrin without being substantially limited by peculiarities of fibrin cross-linking. Accordingly, fibrin is considered to be an MMP substrate according to the invention. Thus, fibrin which occurs naturally in a subject is suitable for degradation according to the invention, as is fibrin induced in vitro. Thus, clots which are induced in blood ex vivo, e.g., in a blood sample, can be degraded according to the invention. In such in vitro applications, a fibrinolytic metalloproteinase can be employed as a coating on a container such as blood collection tube. Also, artificial fibrin, formed from natural, synthetic, semisynthetic, recombinant and/or other types of fibrinogen can also be degraded by the method described herein.

Under physiologic conditions, plasmin is the central enzyme which acts to degrade fibrin. Plasmin action is restricted to the site of fibrin deposition by plasma control mechanisms that prevent proteolysis of circulating proteins. However, under pathologic conditions, plasmin is known to degrade plasma proteins, especially fibrinogen.

Degraded fibrinogen can be separated by ion-exchange chromatography into five fractions (A, B, C, D, and E), of which fragments D and E are the major end products of the original molecule. The identification and characterization of the transient intermediate fragments X and Y engendered the insight for the development of an asymmetric scheme of fibrinogen degradation (Francis et al. 1994).

Classically, fibrinogen structure is bilaterally symmetrical, including a central globular domain E which is a "knot" made up of the N-terminal regions of all six chains in the fibrinogen molecule. From E extend two coiled coils, each containing portions of one set of Aα, Bβ, and γ chains. At the other ends of the coiled coils are globular domains D. Extending from the D domains, are the Aα chain extensions, which, in the $\alpha_E$ subunit only, terminate in another globular domain.

Under proteolytic attack by plasmin, initial cleavages liberate the carboxy-terminal, polar appendage of the Aα chain, and a peptide from the N-terminal portion of the Bβ chain (Bβ1-42). The remaining major fragment is Fragment X. Cleavages of all three polypeptide chains along one coiled coil connecting the central N-terminal knot (E) and a terminal (D) domain of fragment X split it asymmetrically. The result is one fragment D molecule, which consists of carboxy-terminal portions of the three chains, and a fragment Y moiety, consisting of central and terminal domains still connected by a coiled coil. Subsequent cleavage of the coiled coil of fragment Y produces a second fragment D and a fragment E moiety. Fragment X is slowly coagulable by thrombin, but fragments Y and D have potent antipolymerizing effects, due mostly to disruption of the proper alignment and continuation of build-up of the protofibrils of fibrin.

Knowledge of the conventional fragmentation of fibrinogen assists in providing a conceptual framework against which to compare the activity of other potential fibrinolytic enzymes. Moreover, antibodies have been developed which are specifically reactive with or specifically bind to only some of the fragments, thereby permitting molecular identification of fragments with great accuracy and precision (Kudryk et al. 1989a).

To more easily identify enzymatic degradation products of fibrin(ogen), and particularly MMP-3- and other MMP-mediated degradation products of fibrin(ogen), we have searched for antibodies which: (1) react with such degradation products, but (2) fail to react with intact fibrinogen or plasmin digests of fibrin(ogen). This invention concerns the production of a hybridoma which secretes a monoclonal antibody that is reactive with Fragments D/D-dimer generated by MMP-3 and -7 degradation of human fibrin(ogen). In particular, the monoclonal antibody of the invention is specifically reactive with an epitope defined by the amino acid sequence DLWQK (SEQ ID NO:1). This sequence has been identified as constituting a part of the Bβ chain of fibrinogen, specifically Bβ 123-127.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional, albeit not inconsistent, interpretations can be implied.

An "antibody" in accordance with the present specification is defined broadly as a protein that binds specifically to an epitope. The antibodies are monospecific, preferably monoclonal. Monoclonal antibodies may be produced by methods known in the art. These methods include the immunological method described by Köhler and Milstein (1975) and by Campbell (1985); as well as the recombinant DNA method described by Huse et al. (1989).

As used herein, the term "monospecific antibody" refers to any homogeneous antibody or antigen-binding region thereof which is reactive with, preferably specifically reactive with, a single epitope or antigenic determinant. The term "monospecific antibody", most commonly refers to a monoclonal antibody, also abbreviated "MoAb", as that term is conventionally understood. The term "monospecific antibody" as used herein may, however, refer to homogeneous antibodies which are native, modified, or synthetic, and can include hybrid or chimeric antibodies. The term does not include "polyclonal antibodies" as that term is commonly understood.

Use of the term "monospecific" in connection with the present invention should not be construed to limit the antibody to reactivity with only a single chemical moiety. The antibody has been found to be specifically reactive with a specific epitope found on a plurality of structurally related protein moieties, including fragments of fibrinogen and fibrin, most notably enzymatic cleavage fragments of these proteins. The term "anti-Fb" refers to the ability of the monospecific antibody of the invention to react specifically with enzymatic cleavage fragments of fibrin(ogen).

The term "antigen-binding region" refers to a naturally occurring, modified, or synthetic fragment of a monospecific antibody of the invention which is reactive with an epitope of fibrin(ogen) cleavage fragments. Such antigen-binding regions include, but are not limited to, Fab, F(ab')$_2$, and Fv fragments.

Functional equivalents of the antibody of the invention further include fragments of antibodies that have the same binding characteristics as, or that have binding characteristics comparable to, those of the whole antibody. Such fragments may contain one or both Fab fragments or the F(ab')$_2$ fragment. Preferably, the antibody fragments contain all six complement determining regions ("CDRs") of the whole antibody, although fragments containing fewer than all of such regions, such as three, four or five CDRs, may also be functional. Fragments may be prepared by methods described by Lamoyi et al. (1983) and by Parham (1983).

The antibody of the invention is monospecifically reactive with the epitope defined by the amino acid sequence defined by SEQ ID NO:1, and other functionally equivalent sequences, i.e., those amino acid sequences that exhibit similar binding capacities. The antibody is not significantly cross-reactive with moieties lacking the defining epitope. Accordingly, the antibody of the invention is expected to react with other proteins which include within their primary structure the amino acid sequence defined by SEQ ID NO:1. Such proteins may be naturally occurring, such as fibrin I, fibrin II or cross-linked fibrin, or synthetic, e.g., produced by conventional synthetic or recombinant methods such as are known in the art. Homologs of SEQ ID NO:1 and proteins containing this sequence are also expected to be reactive with the antibody of the invention. However, the antibody exhibits no substantial cross-reactivity with moieties lacking this epitope. Moreover, the antibody of the invention completely lacks reactivity with non-denatured or non degraded fibrinogen. This implies that the epitope defined by SEQ ID NO:1 is hidden (occluded) in the intact molecule.

The term "fibrin(ogen)" is intended to include any type of fibrinogen or fibrin. Fibrin(ogen), therefore, refers to monomeric and dimeric fibrinogen molecules having the monomer structure (AαBβγ), as well as molecules having the monomer structure (Aα$_E$Bβγ), and other hybrid molecules, whether naturally occurring, modified, or synthetic. Fibrin (ogen) also refers to polymers of fibrin, formed by polymerization following cleavage of fibrinogen by thrombin. The term "fibrin(ogen)" refers generally to human fibrinogen and fibrin, but may include fibrinogen and fibrin of any species, especially mammalian species. Artificial heterodimers of fibrinogen, as well as recombinant forms are also within the meaning of fibrin(ogen) as employed herein.

It is known in the art that monoclonal antibodies are, in general, difficult to produce. For example, it has been estimated that more than 1,000 clones need to be screened to find one or two antibodies which are specific enough and exhibit enough affinity with the antigen to permit use. These difficulties stem from problems such as irreproducibility of an initial positive screen, or failure to obtain subclones in the first cloning. Such problems are commonly related to the deaths of cells, instability in cell lines, low antibody yield in ascites, instability of antibody, etc.

Generally, to be useful as an immunogen, a peptide fragment must contain sufficient amino acid residues to define the epitope of the molecule being detected. If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule.

Nonetheless, despite these difficulties, the present invention provides hybridoma cell lines which produce monoclonal antibodies reactive with an epitope of a fibrin(ogen) fragment. More generally, the hybridoma cell lines of the invention produce monoclonal antibodies specifically reactive with proteins comprising the amino acid sequence defined by SEQ ID NO:1. The antibodies produced by these hybridomas are also important aspects of the invention.

The hybridoma technology originally described by Köhler and Milstein (1975) can be used to prepare hybridoma cell lines whose secretory product, monoclonal antibodies, are reactive with an epitope or antigenic determinant of fibrin(ogen) fragments comprising the amino acid sequence defined by SEQ ID NO:1. A general method of preparing these hybridoma cell lines of the invention is described below. Further detail concerning the method is provided in the Examples, which relate the construction of a specific hybridoma cell line. Those skilled in the art will recognize that the present invention, including the monoclonal antibodies and hybridoma cell lines described in detail herein, provide a variety of ways to make the hybridomas, and thus the antibodies of the invention.

Hybridoma cell lines of the invention can be prepared using fibrin(ogen) fragments, e.g., matrix metalloproteinase-mediated digestion fragments of fibrin(ogen) as immunogenic material for activation of immunologically relevant spleen cells. Generally, a host mammal is inoculated with a peptide or peptide fragment as described above, and then boosted. Spleens are collected from inoculated mammals a few days after the final boost. Antibody-producing spleen cells, are then harvested and immortalized by fusion with mouse myeloma cells. The hybrid cells, called hybridomas, are continuous cell lines resulting from the fusion, which are then selected and screened for reactivity with the peptide. The artisan is referred to Köhler and Milstein (1975); Kennett et al. (1980); and Goding (1986) for further details on hybridoma technology. See also Campbell (1985).

The anti-Fb monospecific antibodies described herein are merely illustrative of the invention, and all monospecific antibodies which are specifically reactive with enzymatic cleavage fragments of fibrin(ogen), regardless of species of origin or immunoglobulin class or subclass designation, including IgG, IgA, IgM, IgE, and IgD, are included in the scope of this invention. The present invention also provides antigen-binding fragments of the anti-Fb antibodies. The ability to bind to fibrin(ogen) fragments comprising the amino acid sequence defined by SEQ ID NO:1 is a general characteristic of monospecific antibodies according to the invention.

As discussed above, monospecific antibodies of the invention can be constructed and isolated by immunization of animals, preparation of hybridomas, and identification of antibodies with a reactivity to fibrin(ogen) fragments similar to that of the anti-Fb antibodies described. However, the present invention also provides means for identifying monospecific antibodies of the invention that does not require determination of antibody reactivity with a broad number of Bβ-chain-related fragments. Antibodies of the invention can be identified also by immunoprecipitation and competitive binding studies using the antibody produced by the cell lines described herein.

Immunoprecipitations using the anti-Fb monospecific antibody can be used to determine antigenic identity. Confirmation of identity can be obtained by depleting the antigen from testable samples such as plasma samples, using excess amounts of one anti-Fb antibody and observing the inability of another antibody to immunoprecipitate a Bβ-chain fragment from the treated sample. Also, in instances in which the antibodies bind with the same epitope or closely associated epitopes, each antibody will compete with the other(s) for binding to the particular fibrin(ogen) fragments. Competitive binding studies are generally known in the art, and one conventional type is presented in the examples below.

Treatment of antibody preparations with proteolytic enzymes such as papain and pepsin generates antibody fragments, including the Fab and F(ab')$_2$ species, which retain antigen-binding activity. Treatment of the antibodies of the invention with such enzymes can therefore be used to generate antigen-binding fragments of the invention. The preparation of antigen-binding fragments of the antibodies of the invention and their diagnostic and therapeutic usefulness, as well as other applications, suggest themselves to the skilled artisan. Antigen-binding fragments of the anti-Fb antibody are especially useful in diagnostic embodiments of the present invention.

Those skilled in the art will recognize that the antigen-binding region of the antibodies and antibody fragments of the invention is a key feature of the present invention. The anti-Fb hybridoma cells of the invention serve as a preferred source of DNA that encodes such antigen-binding regions of the invention. This DNA, through recombinant DNA technology, can be attached to DNA that encodes any desired amino acid residue sequence to yield a novel "hybrid," or "chimeric," DNA sequence that encodes a hybrid, or chimeric, protein. In such a fashion, chimeric antibodies of the invention, in which one portion of the antibody is ultimately derived from one species and another portion of the antibody is derived from another species, can be obtained. However, the present invention also comprises any chimeric molecule that contains an antigen-binding region.

Antibodies of the present invention can also be labeled by conjugation to any detectable group, such as fluorescent labels, enzyme labels, and radionuclides to identify expression of cleavage products of fibrin(ogen). Suitable detectable labels may be selected from among those known in the art, including, but not limited to, radionuclides, enzymes, specific binding pair components, colloidal dye substances, fluorochromes, reducing substances, latexes, digoxigenin, metals, particulates, dansyl lysine, antibodies, protein A, protein G, electron dense materials, chromophores, and the like. Effectively, any suitable label, whether directly or indirectly detectable, may be employed. One skilled in the art will clearly recognize that these labels set forth above are merely illustrative of the different labels that could be utilized in this invention.

Methods for labeling antibodies have been described, for example, by Hunter and Greenwood (1962) and by David et al. (1974). Additional methods for labeling antibodies have been described in U.S. Pat. Nos. 3,940,475 and 3,645,090.

The label may be radioactive, i.e., contain a radionuclide. Some examples of useful radionuclides include $^{32}P$, $^{125}I$, $^{131}I$, $^{111}In$, and $^{3}H$. Use of radionuclides have been described in U.K. patent document No. 2,034,323, U.S. Pat. Nos. 4,358,535, and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophoric molecules may be conjugated to the antibodies by means of coupling agents, such as dialdehydes, carbodiimides, dimaleimides, and the like.

The label may also be conjugated to the antibody probe by means of a ligand attached to the probe by a method described above and a receptor for that ligand attached to the label. Any of the known ligand-receptor combinations is suitable. Some suitable ligand-receptor pairs include, for example, biotin-avidin or -streptavidin, and antibody-antigen. The biotin-avidin combination is preferred. Thus, the anti-Fb antibodies of the invention can be derivatized by conjugation to biotin, and used, upon addition of species of avidins which have been rendered detectable by conjugation to fluorescent labels, enzyme labels, radionuclides, electron dense labels, substrates, etc., in a multiplicity of immunochemical and immunohistological applications.

The monospecific antibodies of the invention may also be attached or bound to substrate materials according to methods known to those skilled in the art. Such materials are generally substantially solid and relatively insoluble, imparting stability to physical and chemical disruption of the antibodies, and permitting the antibodies to be arranged in specific spatial distributions. Among substrate materials, materials may be chosen according to the artisan's desired ends, and include materials such as gels, hydrogels, resins, beads, nitrocellulose, nylon filters, microtiter plates, culture flasks, polymeric materials, and the like, without limitation.

The monospecific antibodies of the present invention, whether labeled or unlabeled, can be used in immunological assays to determine the presence of fibrin(ogen)-associated peptides in tissue samples from human or animal subjects. Biopsy and necropsy samples of subjects, as well as samples from tissue libraries or blood banks, can be evaluated for the presence of fibrin(ogen) fragments using an anti-Fb antibody of this invention. Moreover, suitable pharmaceutical preparations according to the invention may be employed for in vivo use, such as for the visualization of such fibrin(ogen) fragments and structures in a living subject.

Thus, the invention provides a method for binding enzymatic cleavage fragments of fibrin(ogen) comprising the amino acid sequence defined by SEQ ID NO: 1 by means of the anti-Fb monospecific antibody. Accordingly, plasmin, matrix metalloproteinase, and other enzymatic cleavage products of fibrin and fibrinogen, as well as natural, modified, and synthetic variants thereof, may be detected and measured by means of monospecific antibodies of the invention.

In the fibrinogen binding method of the invention, the method includes contacting a testable system, in which the presence or absence of fibrinogen is to be determined, with a composition comprising an anti-Fb monospecific antibody or antigen-binding region thereof. The method then involves measuring an amount of specific association or binding between the testable system and the monospecific antibody. In this method, specific binding of the antibody in the system indicates the presence of fibrin(ogen) fragment in the system. The testable system may be either in vivo or in vitro, and the method of the invention may be performed in vivo, in vitro, or a combination thereof.

The present invention further provides a method of detecting the presence of digestion products of fibrin(ogen) in a sample. The method involves use of a labeled probe that recognizes protein present in a biological sample such as a blood sample. The probe may be an antibody that recognizes protein present in the sample, or a fragment thereof.

The invention also provides a diagnostic method for the characterization of fibrin(ogen). In this method, a biological sample such as a body fluid is contacted with an antibody according to the invention to permit the detection of fibrinogen degradation products.

A typical method involves the differential separation of degradation products, such as separation of the products by gel electrophoresis. The products are then measured by contacting the products with antibodies which are specifically reactive with or specifically associate with one or more domains of fibrinogen. A number of such antibodies are described by Kudryk et al. (1 989a). Preferably, such antibodies are specifically reactive with a single degradation product, thereby permitting characterization of the product in relation to other products.

In a preferred embodiment, the detection method employs a monospecific antibody which has been detectably labeled with a marker moiety. In other embodiments, the method may employ a monospecific antibody of the invention which has been bound to a substrate material. In the method, the composition may also include other reagents such as other antibodies which differentially detect other fibrinogen subunits or subtypes. This method can be further adapted for use with at least one other antibody having specificity for alternative fragments, permitting differential analysis or characterization of fibrin(ogen) and various fragments thereof in the same sample. For example two or more antibodies conjugated to distinct fluorescent labels can be employed as probes in protein separations or other immunometric techniques.

The fibrin(ogen)-fragment binding method of the invention includes methods known in the art which employ antibodies to specifically bind target substances. Preferred methods include immunochemical methods, such as enzyme-linked immunosorbent assay (ELISA) methods, immunonephelometry methods, agglutination methods, precipitation methods, immunodiffusion methods, immunoelectrophoresis methods, immunofluorescence methods, and radioimmunoassay methods.

Assays for detecting the presence of proteins with antibodies have been previously described, and follow known formats, such as standard blot and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

The standard ELISA protocol is exemplary, and is described, for example, by Kennett et al. (1980). Briefly, plates are coated with antigenic protein at a concentration sufficient to bind detectable amounts of the antibody. After incubating the plates with the protein, the plates are blocked with a suitable blocking agent, such as, for example, 10% normal goat serum. The sample, such as patient sera, is added and titered to determine the endpoint. Positive and negative controls are added simultaneously to quantitate the amount of relevant antibody present in the unknown samples. Following incubation, the samples are probed with goat anti-human Ig conjugated to a suitable label, such as an enzyme. The presence of anti-protein antibodies in the sample is indicated by the presence of the label.

In a preferred embodiment, a protein is immobilized on a solid support through an immobilized first antibody specific for the protein. The immobilized first antibody is incubated with a sample suspected of containing the protein. If present, the protein binds to the first antibody.

A second antibody, also specific for the protein, binds to the immobilized protein. The second antibody may be labeled by methods known in the art. Non-immobilized materials are washed away, and the presence of immobilized label indicates the presence of the protein. This and other immunoassays are described in U.S. Pat. No. 4,376,110.

Immunoassays may involve one step or two steps. In a one-step assay, the target molecule, if it is present, is immobilized and incubated with a labeled antibody. The labeled antibody binds to the immobilized target molecule. After washing to remove unbound molecules, the sample is assayed for the presence of the label.

In a two-step assay, immobilized target molecule is incubated with an unlabeled first antibody. The target molecule-antibody complex, if present, is then bound to a second, labeled antibody that is specific for the unlabeled antibody. The sample is washed and assayed for the presence of the label, as described above.

The immunometric assays described above include simultaneous sandwich, forward sandwich, and reverse sandwich immunoassays. These terms are well known to those skilled in the art.

In a forward sandwich immunoassay, a sample is first incubated with a solid phase immunoabsorbent containing antibody against the protein. Incubation is continued for a period of time sufficient to allow the protein in the sample to bind to the immobilized antibody in the solid phase. After the first incubation, the solid phase immunoabsorbent is separated from the incubation mixture and washed to remove excess protein and other interfering substances which also may be present in the sample. Solid phase immunoabsorbent-containing protein bound to the immobilized antibodies is subsequently incubated for a second time with soluble labeled antibody cross-reactive with a different domain on the protein. After the second incubation, another wash is performed to remove the unbound labeled antibody from the solid immunoabsorbent and to remove non-specifically bound labeled antibody. Labeled antibody bound to the solid phase immunoabsorbent is then detected and the amount of labeled antibody detected serves as a direct measure of the amount of antigen present in the original sample. Alternatively, labeled antibody that is not associated with the immunoabsorbent complex can also be detected, in which case the measure is in inverse proportion to the amount of antigen present in the sample. Forward sandwich assays are described, for example, in U.S. Pat. Nos. 3,867,517, 4,012,294, and 4,376,110.

In a reverse sandwich assay, the sample containing the antigen is initially incubated with labeled antibody. A solid-phase immunoabsorbent containing an immobilized antibody that is cross-reactive with a different domain on the antigen is added to the labeled antibody/sample mixture, and a second incubation is carried out. The initial washing step required by a forward sandwich assay is not required, although a wash is performed after the second incubation. Reverse sandwich assays have been described, for example, in U.S. Pat. Nos. 4,098,876 and 4,376,110.

In a simultaneous sandwich assay, the sample, the immunoabsorbent with immobilized antibody, and labeled soluble antibody specific to a different domain are incubated simultaneously in one incubation step. The simultaneous assay requires only a single incubation and does not require any washing steps. The use of a simultaneous assay is a very useful technique, providing ease of handling, homogeneity, reproducibility, linearity of the assays, and high precision. See, e.g., U.S. Pat. No. 4,376,110.

In each of the above assays, the sample containing antigen, solid phase immunoabsorbent with immobilized antibody and labeled soluble antibody are incubated under conditions and for a period of time sufficient to allow antigen to bind to the immobilized antibodies and to the soluble antibodies. In general, it is desirable to provide incubation conditions sufficient to bind as much antigen as possible, since this maximizes the binding of labeled antibody to the solid phase, thereby increasing the signal. The specific concentrations of labeled and immobilized antibodies, the temperature and time of incubation, as well as other such assay conditions, can be varied, depending upon various factors including the concentration of antigen in the sample, the nature of the sample and the like. Those skilled in the art will be able to determine operative and optimal assay conditions for each determination by employing routine experimentation.

There are many solid phase immunoabsorbents which have been employed and which can be used in the present invention. Well known immunoabsorbents include beads formed from glass, polystyrene, polypropylene, dextran, nylon, and other material; and tubes formed from or coated with such materials, and the like. The immobilized antibodies may be covalently or physically bound to the solid phase immunoabsorbent, by techniques such as covalent bonding via an amide or ester linkage or by absorption.

The invention further includes a method for determining or diagnosing the existence of or probability of thrombogenesis or atherogenesis in a subject. Alternatively, the method includes the detection and localization of fibrotic or atherosclerotic plaques and/or lesions. In this method, an amount of an analyte (e.g., a fibrinogen fragment thereof comprising SEQ ID NO:1) is measured by means of a composition including an anti-Fb monospecific antibody of the invention. The measured amount of the fibrinogen-related analyte is compared with an amount of the analyte which is recognized or known to be associated with thrombogenesis or atherogenesis. The method then involves the determination from the measured and standard value(s) of the presence or likelihood of thrombogenesis or atherogenesis in the subject. The method can include measuring or detecting fibrinogen fragments containing Bβ123-127 in vivo, such as by imaging or visualizing the location and/or distribution of such fragments in the body. Alternatively, the method includes obtaining a medical sample from the subject and measuring fibrinogen ex vivo or in vitro. This method preferably involves the differential measurement of at least two epitopes of fibrinogen, including the Bβ123-127 epitope.

The invention also includes a method for fractionation of fibrinogen fragments comprising SEQ ID NO:1. Such methods include contacting a medical sample containing fibrinogen fragments with a composition of the invention which includes an anti-Fb monospecific antibody. Preferably, the method is performed using conditions which are conducive to binding of fibrinogen fragments with the monospecific antibody. Then the bound fibrinogen fragments are removed from the sample. The method is represented by chromatography-type methods, both preparative and analytical. Numerous such methods are known in the art and can be selected by the artisan as desired. In this method, the monospecific antibody may be soluble, suspended in fluid phase, or attached to a substantially solid phase, as desired.

The invention further includes a method for purifying fibrin(ogen) fragments comprising the amino acid sequence defined by SEQ ID NO:1. For purifying or separating such proteins from other components of biological samples, the method can comprise contacting a sample containing Bβ123-127 fragment of fibrin(ogen) with a composition comprising a monospecific antibody which binds specifically with the fibrinogen fragment, under conditions conducive to binding of the antibody with the fibrinogen fragment. Then, the fibrinogen fragments are selectively removed from the antibody. In the method, the monospecific antibody can be soluble, e.g., suspended in a fluid phase, or it can be attached to a solid phase or substrate.

The invention further provides diagnostic and experimental kits which include anti-Fb monospecific antibodies, and enable the detection, purification and/or separation fibrinogen fragments in a specific and reproducible manner. In these kits, the antibodies may be provided with means for binding to detectable marker moieties or substrate surfaces. Alternatively, the kits may include the antibodies already bound to marker moieties or substrates. The kits may further include positive and/or negative control reagents as well as other reagents for adapting the use of the antibodies of the invention to particular experimental and/or diagnostic techniques as desired. The kits may be prepared for in vivo or in vitro use, and may be particularly adapted for performance of any of the methods of the invention, such as ELISA. For example, kits containing antibody bound to multi-well microtiter plates can be manufactured.

The invention also provides a diagnostic method for the characterization of fibrin(ogen). In this method, fibrin(ogen) is contacted with an endogenous matrix metalloproteinase, preferably MMP-3, to produce degradation products. The degradation products are then analyzed to determine the types and amounts of cleavage products generated by the activity of the MMP.

Typically, the method involves the differential separation of degradation products, such as separation of the products by gel electrophoresis. The products are then measured such as by non-specific staining to reveal quantities of products of different sizes. Alternatively, the products can be identified by contacting the products with antibodies which are specifically reactive with or specifically associate with one or more domains of fibrin(ogen) (Kudryk et al. 1989a). Preferably, such antibodies are specifically reactive with a single degradation product, thereby permitting characterization of the product in relation to other products.

In one such embodiment, an endogenous fibrinolytic MMP, preferably MMP-3, is bound to a substrate material such as a membrane, blood collection tube, microtiter plate, culture flask, or the like. In this manner, the method of the invention can be performed in the absence of soluble MMP, to induce fibrin(ogen)olysis in a fluid sample. Alternatively, this approach is useful in coating membranes and prosthetic devices.

The following examples are intended to assist in a further understanding of the invention. The particular materials and conditions employed are intended to be further illustrative of the invention and are not limiting upon the reasonable scope thereof.

The following experimental procedures are relevant to Examples 1–11, below:

Proteins and Other Reagents. Plasminogen-free and fibronectin-free Fg (Fg≧95% clottable) or lyophilized human Fg were purchased (American Diagnostica Inc., Greenwich, Conn.). Plasminogen and fibronectin were removed by affinity chromatography on lysine-Sepharose and gelatin-Sepharose, essentially as described by others (Deutsch et al. 1970; Engvall et al. 1977; Procyk et al. 1985). The amount of Factor XIII in these preparations is 0.1–0.2 Loewy units/mg of Fg according to the manufacturer. Stock solutions of Fg (12 mg/mL in TNE buffer (0.05 M Tris-HCl (pH 7.4), containing 0.1 M NaCl, 0.001 M EDTA and 100 KIU/mL aprotinin)) were stored at −70° C. until used. Fg concentration was measured spectrophotometrically in alkaline-urea using extinction coefficient (1%, 1 cm)=16.5 at 282 nm. Aprotinin was from Mobay Chemical Corp (New York, N.Y.). Human α-thrombin (2300 U/mg) was obtained as a gift. All other reagents were of analytical grade and were purchased from Fisher Scientific (Springfield, N.J.).

Gel electrophoresis/Immunoblotting. Samples of Fg and XL-Fb degraded with plasmin or MMPs were subjected to SDS-PAGE using both reducing and non-reducing conditions. Reduced samples were prepared in 62.5 mM Tris buffer, pH 6.8, containing 4% SDS, 8 M urea, 5% DTT, 10% glycerol and 1% bromphenol blue. Non-reduced samples were made in the same buffer without DTT. SDS-PAGE was performed using 5–15% gradient or 12.5% polyacrylamide gels in Tris-glycine buffer (Laemmli 1970) or with 5% and 7.5% mini gels in phosphate buffer (McDonagh et al. 1972) following general procedures. Prestained molecular weight standards used were myosin (200 kDa), phosphorylase B (97.4 kDa), BSA (68 kDa), ovalbumin (43 kDa), α-chymotrypsinogen (25.7 kDa), β-lactoglobulin (18.4 kDa) and lysozyme (14.3 kDa) (Bethesda Research Laboratories, Gaithersburg, Md.).

Transfer to nitrocellulose membranes for immunoblot analyses was performed as described by Towbin et al. (1979) with few modifications (Kudryk et al. 1989b). In some experiments, membranes were stained with colloidal gold prior to immunoblotting (Colloidal Gold Total Protein Stain, BioRad, Hercules, Calif.). Membranes were blocked with 5% dry milk (Carnation, Nestle, Glendale, Calif.) or with 5% BSA, incubated overnight with a selected primary antibody and then probed with a second antibody conjugated to rabbit anti-mouse-horseradish peroxidase (RAM-HRPO), prepared as described by Goding (1986) using RAM purchased from Dako (Carpinteria, Calif.) and HRPO (type VI) from Sigma. Bound peroxidase complexes were detected using the chemiluminescent substrate Luminol (ECL Western blotting detection system, Amersham Life Science, Arlington Heights, Ill.). Light emitted from the hydrolysis of the added Luminol substrate exposed the provided film (Kodak χ-Omat RP, Eastman Kodak Company, Rochester, N.Y.) in 10 to 30 seconds.

EXAMPLE 1

Preparation of Hybridoma and Isolation of Monoclonal Antibody T54-2

A monoclonal antibody was isolated from the hybridoma cell line designated "T54-2." This antibody was isolated from a fusion experiment using spleen cells of an animal sensitized with reduced/alkylated chains of tissue transglutaminase (ti-TG) crosslinked fibrinogen (Kudryk et al. 1993). In using this immunogen we had hoped to identify antibodies specific for fibrinogen cross-linked by this transglutaminase but not by Factor XIIIa, the plasma transglutaminase which is responsible for stabilizing fibrin clots. Instead, we obtained MoAb/T54-2 (IgG1, κ isotype) which has unexpectedly been found to be suitable for distinguishing certain MMP digest products from corresponding fragments obtained by cleavage with plasmin.

Immunization and Production of Hybridomas

Immunization with reduced and alkylated chains of tissue transglutaminase (ti-TG) cross-linked fibrinogen was similar to the protocol used in preparing the fibrinopeptide A (FPA)-specific antibody designated MoAb/8C2-5 (see Kudryk et al. (1989b) and European Patent No. 0 345 811 B1). BALB/c (Jackson Lab, Bar Harbor, Me.) mice were immunized intraperitoneally (i.p.) with the chain mixture (~0.05 mg/animal) mixed with complete Freund's adjuvant. Six subsequent booster injections (i.p.), at two week intervals, consisted of the same immunogen mixed with incomplete Freund's adjuvant. After a four week rest period, the animals were boosted (i.p.) and three days following this final boost, the spleen of the animal showing the highest titer was used for fusion. Serum also was collected from this animal prior to sacrifice. Spleen cells were fused with myeloma cells (P3X63Ag8.653) at a ratio of about 4:1 in 1 mL 50% polyethylene glycol (approx. mol. wt. 4000, VWR Scientific, New York, N.Y.) in RPMI (Sigma, St. Louis, Mo.). The remainder of the fusion ("fulsion by stirring") procedure was identical to that described by Harlow et al. (1988).

Testing of Prefusion/Fusion Antisera and Hybridoma Culture Media

Antisera were used for titer estimation by enzyme-linked immunosorbent assay (ELISA) and also for immunoblot analysis (see below). In the ELISA procedure, microtiter plates were coated with the following: reduced and alkylated chain mixture used as immunogen, HPLC-purified chains derived from the immunogen mixture, intact human fibrinogen, intact human fibrin II, purified plasmin Fragments D and E, respectively, N-DSK+ [the $NH_2$-terminal "disulfide knot" $(A\alpha 1$-$51, B\beta 1$-$190, \gamma 1$-$78)_2$, $M_r$~75,000) of fibrinogen obtained by cleavage with CNBr] before and after digestion with thrombin. Similar plates were also used in screening hybridoma culture media. Coating of polyvinyl microtiter plates (Costar, Cambridge, Mass.), washing, blocking and antibody detection was similar to that described previously (Kudryk et al. 1983).

Whereas polyclonal antisera from animals immunized with the chain mixture bound all plastic-coated antigens tested, the antibody present in T54-2 clone culture media (CCF) reacted with only those structures containing SEQ ID NO:1 (i.e., chain mixture used as immunogen, fibrinogen Bβ-chain/fibrin β-chain, N-DSK+ and to a much lesser degree intact fibrinogen and non-cross-linked fibrin).

Production of Ascites, Purification and Isotyping of Antibody

Since antibody levels in ascites are known to be in the 3–15 mg/mL range, hybridoma cell line T54-2 (see below) was grown in the peritoneal cavity of BALB/c mice using the following protocol. Mice were primed (i.e.) with 0.5 mL Freund's incomplete adjuvant. One day following this stimulation, approximately $10^7$ hybrid cells were injected (i.p.) into animals. Ascites were collected 8–12 days later, filtered on a Millex-PF 0.8 μm filter unit (Millipore Corp, Bedford, Mass.), adjusted to 0.1% with $NaN_3$ and stored frozen (−70° C.) until needed. Antibody titer in ascites was usually estimated by high-performance liquid chromatography (HPLC) using DEAE or BIO-GEL® HPHT columns. Antibody from ascites was purified by chromatography on DEAE columns using standard procedures. The isotype of the purified antibody was determined by ELISA. Polyvinyl microtiter plates were coated with antibody at a concentration of about 0.5 μg/mL in $Na_2CO_3$/$NaHCO_3$, pH 9.6 and screening was accomplished using the ScreenType™ kit and procedure obtained from Boehringer Mannheim (Indianapolis, Ind.).

EXAMPLE 2

Immunoblot Analysis Using MoAb/T54-2

The following samples, after exhaustive reduction with DTT, were electrophoresed (SDS-PAGE, 7% gels): protein markers with indicated kDa (lane 1); fibrinogen (lane 2);

XIIIa cross-linked fibrin (lane 3); N-DSK (lane 4) ("N-DSK" is the N-terminal disulfide knot (Aα 1-51, Bβ1-118, γ1-78)$_2$, 58 kDa, of fibrinogen obtained by cleavage with CNBr). The protein-stained membrane is on the left, and the antibody-reactive bands are in the center and right panels, detected using Luminol as described above.

Antibody P10 (IgG1, κ isotype) is specific for an epitope at the N-terminal end (Bβ1-14) of Fg Bβ-chain. This antibody binds fibrinogen Bβ-chain (lane 2) but, predictably, fails to react with β-chain of fibrin which lacks the segment Bβ1-14. The P10 antibody is described in detail in U.S. pateny application Ser. No. 08/900,660, filed on Jul. 25, 1997 entitled "Monospecific Antibody Reactive with Fibrinogen and Fibrinopeptide B", now U.S. Pat. No. 5,876,947, the entire disclosure of which is incorporated herein by reference.

Figure 1B:
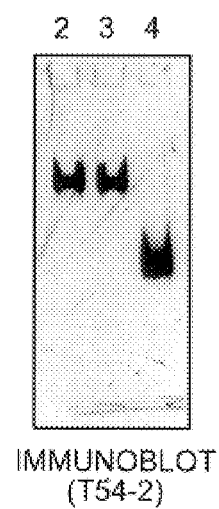
FIG. 1B is an immunoblot of separated proteins using the T54-2 antibody.
Figure 1C:
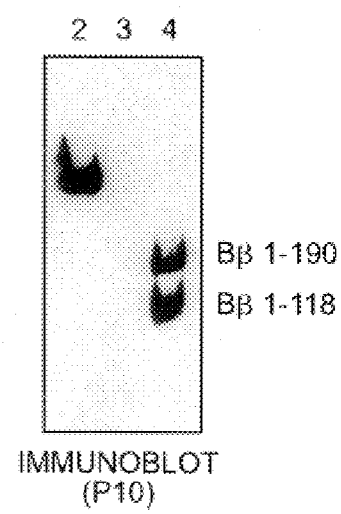
FIG. 1C is an immunoblot of separated proteins using the P10 antibody.

As shown in FIGS. 1A–1C, MoAb/T54-2 is specific for Fg Bβ-chain/XL-Fb β-chain and also reacts with an N-terminal segment of the Fg Bβ-chain (Bβ1-190) present in a subpopulation of N-DSK fragments due to incomplete cleavage by CNBr at the Bβ Met118-Tyr119 bond.

EXAMPLE 3

Binding ELISA Using MoAb/T54-2

Figure 2:
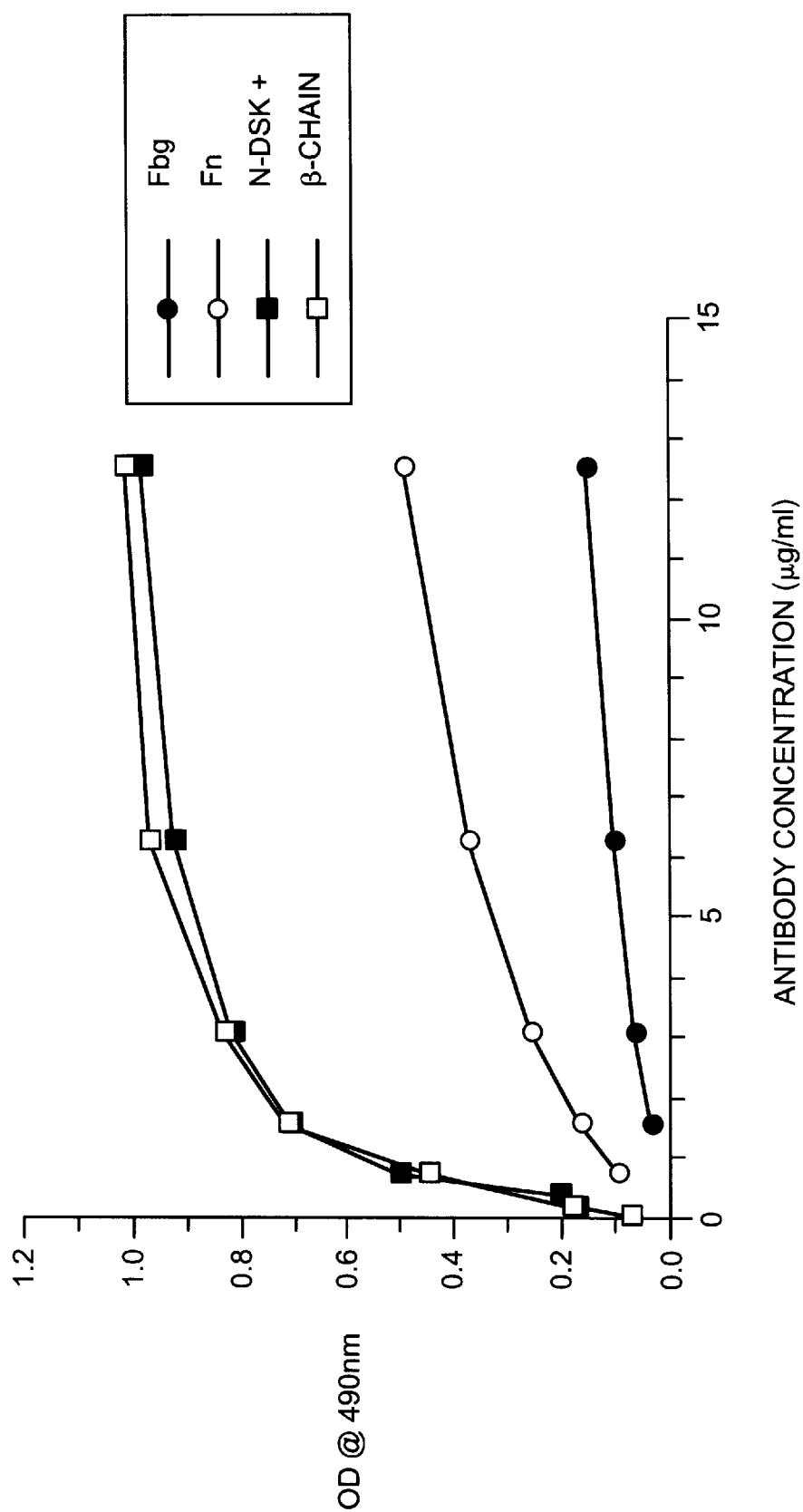
FIG. 2 is a graph illustrating a binding(B)-ELISA experiment, showing comparative binding of the T54-2 MoAb with four fibrinogen-related test ligands.

FIG. 2 is a graph illustrating a (B)-ELISA experiment using four different but related antigens and MoAb/T54-2. All four antigens were coated to Costar (Cambridge, Mass.) 96-well vinyl assay plates at ~20 pmol/mL for 18 hrs at 4° C. Due to problems in solubility in neutral buffers, the stock solution of non cross-linked fibrin (Fn) was 4 mg/mL in 5% acetic acid, N-DSK+ was 2 mg/mL in 5% acetic acid and the fibrin β-chain was 2 mg/mL in 10% acetonitrile/0.1% $H_3PO_4$. Binding of MoAb/T54-2 was performed as described in Example 7 below. These results show that the monospecific antibody of the invention binds very poorly to a plastic plate coated with intact fibrinogen (Fg), somewhat better to non cross-linked fibrin (Fn) but best to both the purified β-chain of fibrin or the N-DSK+ cyanogen bromide (CNBr)-cleaved fragment of fibrinogen. Since this antibody does not compete with intact, soluble fibrinogen (see Example 11), the low level of binding observed with this antibody and surface coated fibrinogen suggests that the epitope (Bβ123-127) reactive with this antibody may become partially exposed as consequence of fibrinogen binding to the vinyl assay plate. The increased level of binding of MoAb/T54-2 to non cross-linked fibrin may be due to the fact that fibrin is stored in acid prior to coating and that this and its subsequent coating to vinyl exposes the Bβ123-127 segment to a much greater degree as compared to that when fibrinogen is coated to a plate from a stock that is stored in a neutral buffer.

EXAMPLE 4

Binding ELISA using MoAb/T54-2 and Plasmin Digests of Fibrinogen

Figure 3A:
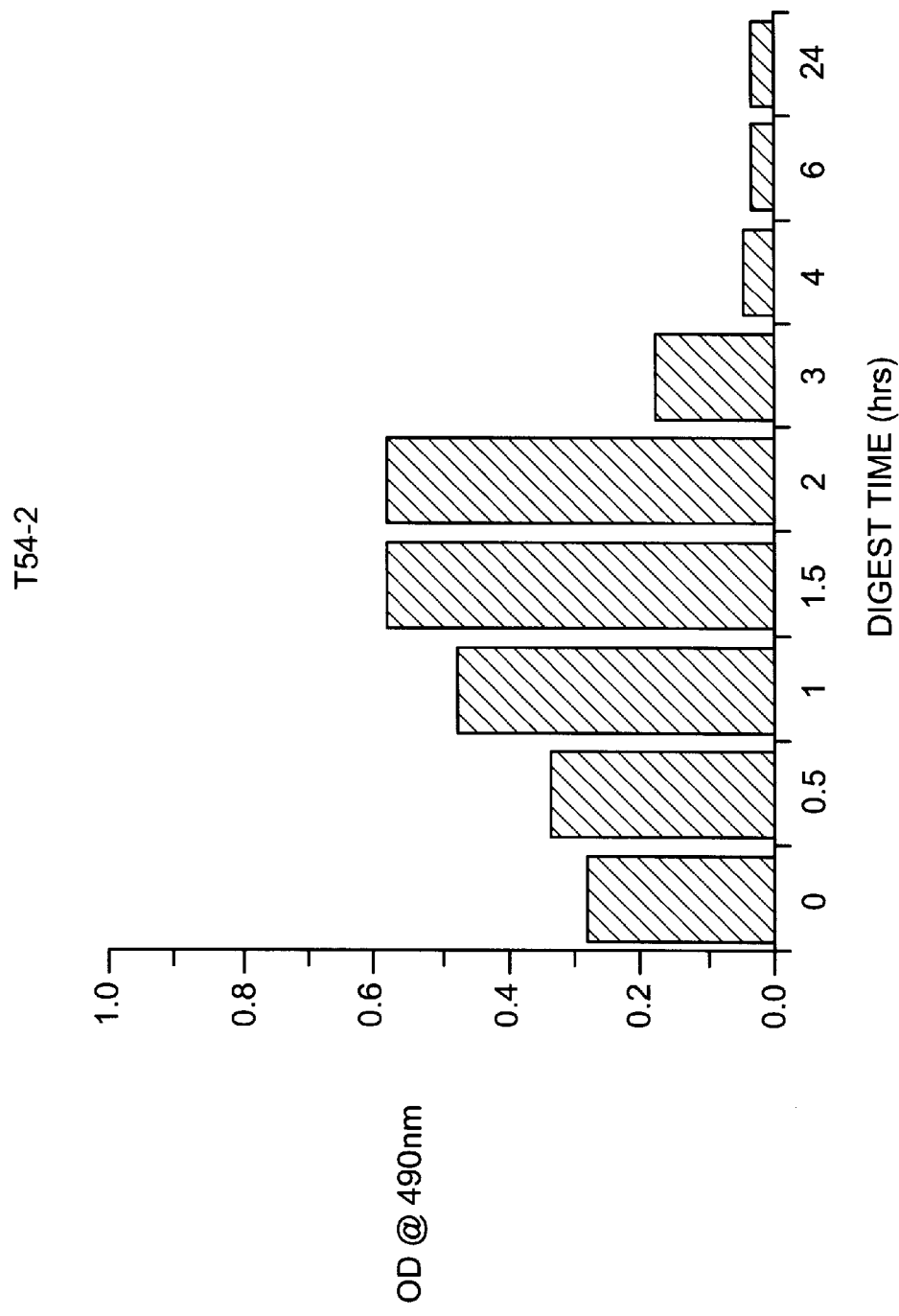
FIG. 3A is a graph illustrating a B-ELISA experiment, showing binding of the T54-2 antibody with intact fibrinogen and plasmin digests of fibrinogen in buffer containing $Ca^{2+}$.
Figure 3B:
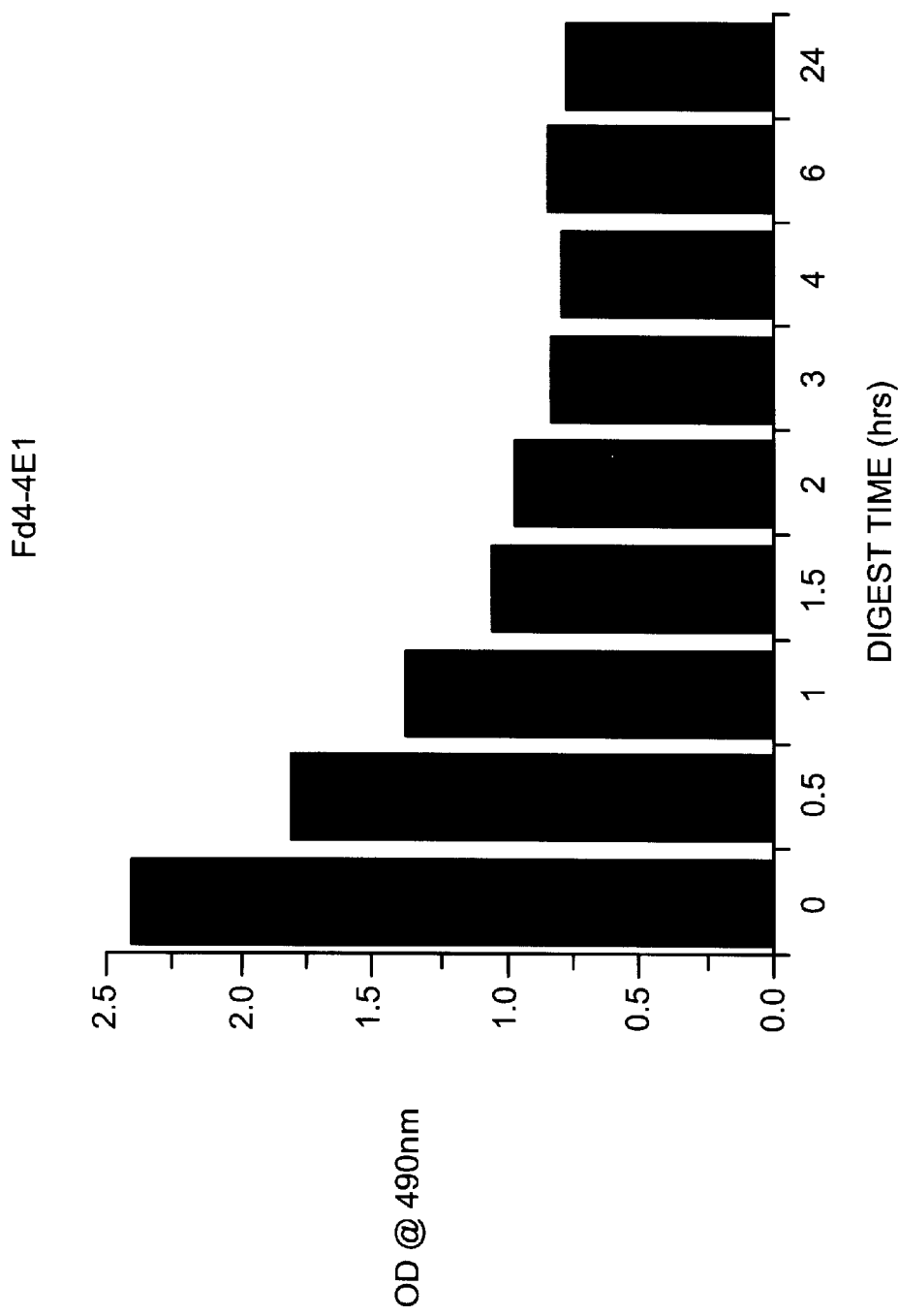
FIG. 3B is a graph showing binding of a different monoclonal antibody (Fd4-4E1) with fibrinogen and the same plasmin digests thereof.

FIG. 3A is a histogram illustrating a (B)-ELISA experiment to determine the binding affinity of the T54-2 antibody for plasmin digests of fibrinogen. The digests were made in a buffer containing 10 mM $CaCl_2$ and were terminated at the indicated time points by addition of aprotinin. Each digest was coated at 8 μg/mL (duplicate wells) and, after appropriate incubation, washing and blocking. 100 μL/well of MoAb/T54-2 at 10 μg/mL was added per well to assess the level of interaction. FIG. 3B illustrates binding with these same digests at similar time points but using a different antibody (Fd4-4E1). The latter antibody reacts with intact fibrinogen and the plasmin-derived core fragment Fg-D$_1$ prepared in buffers containing $Ca^{2+}$.

Figure 4A:
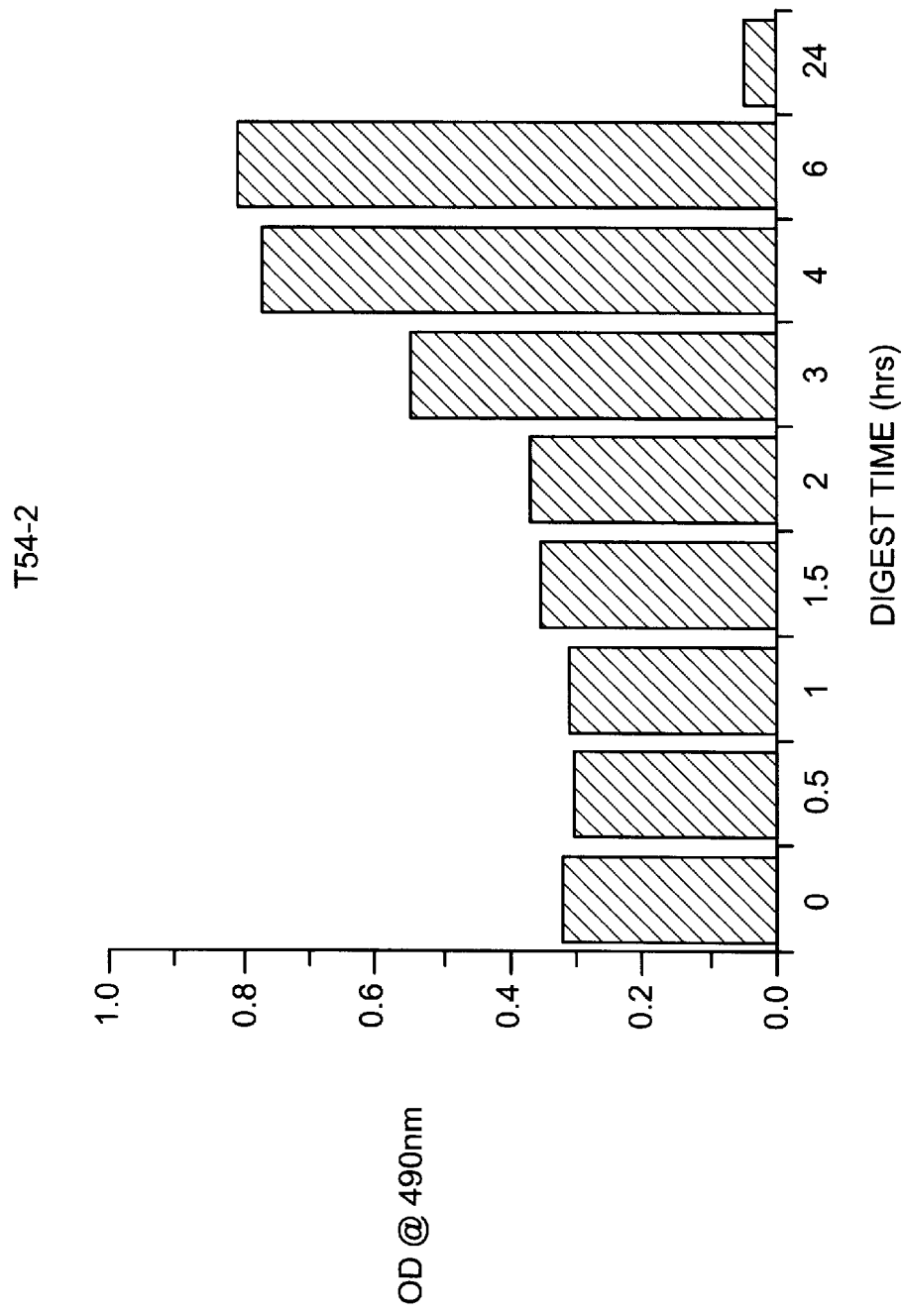
FIG. 4A is a graph illustrating a B-ELISA experiment, showing binding of the T54-2 antibody with intact fibrinogen and plasmin digests of fibrinogen in buffer containing the $Ca^{2+}$ chelator EDTA.
Figure 4B:
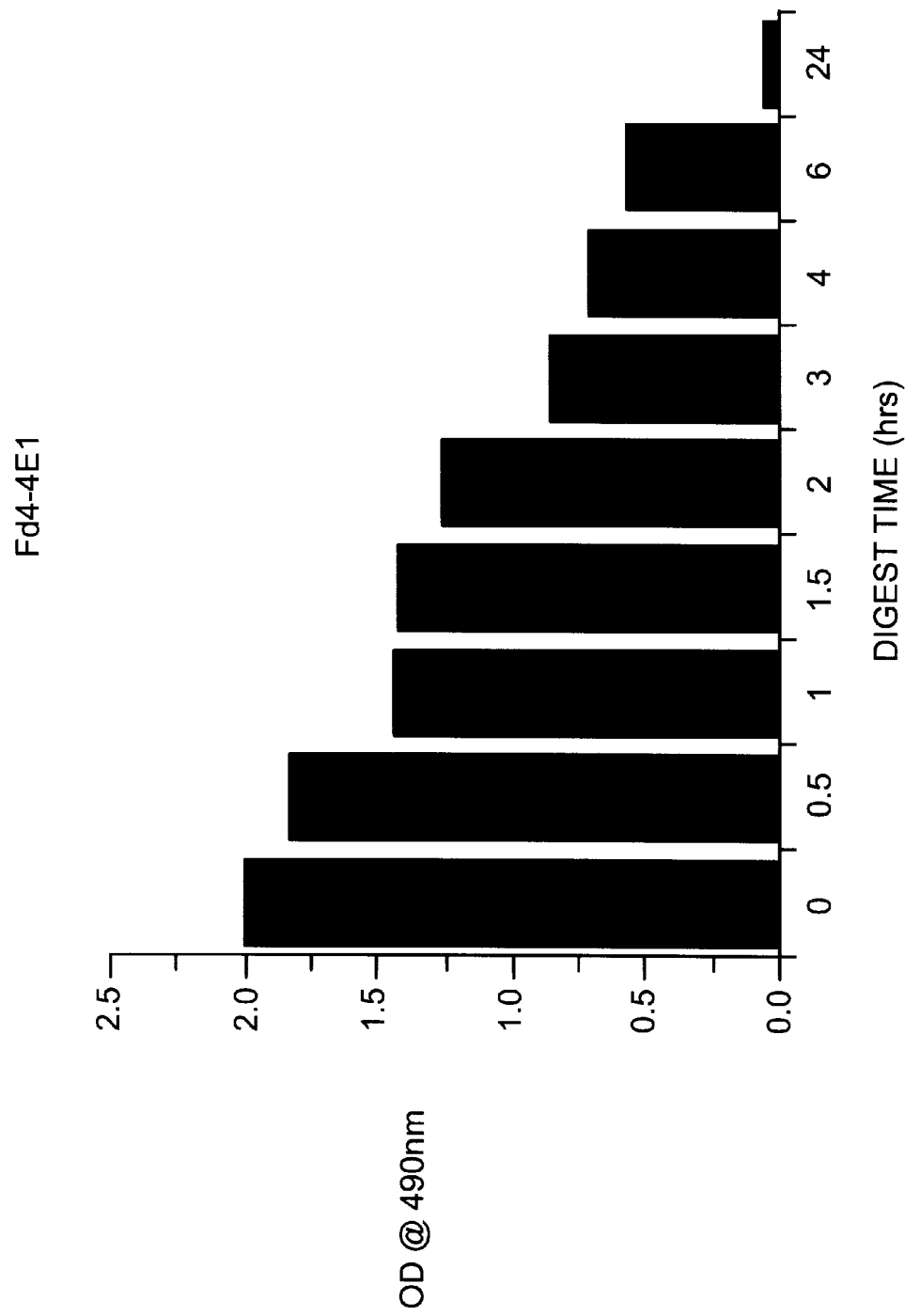
FIG. 4B is a graph showing binding of a different monoclonal antibody (Fd4-4E1) with fibrinogen and the same plasmin digests thereof.

FIG. 4A is a graph illustrating a (B)-ELISA experiment using plasmin digests prepared in 1 mM EDTA of fibrinogen and MoAb/T54-2. Loss of reactivity of this antibody and these digests occurs much more slowly than in those prepared in a buffer containing $Ca^{2+}$ (FIG. 3A). FIG. 4B illustrates the level of binding of these same digests with MoAb/Fd4-4E1. The latter antibody shows only slight binding to a 24 hr digest prepared in EDTA since at this time point little, if any, Fg-D$_1$ remains. Generally, a 24 hr digest contains only Fg-D$_3$, and the Fd4-4E1 antibody fails to react with this small species of Fragment D.

EXAMPLE 5

Immunoblot Analysis using MoAb/T54-2

Figure 5A:
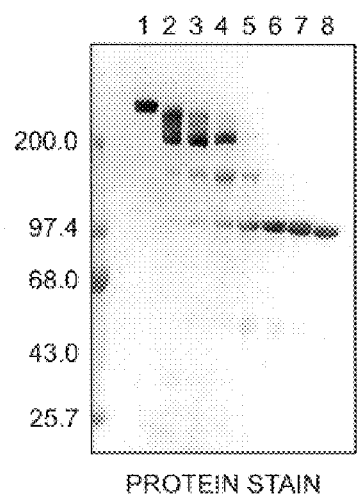
FIG. 5A is an electrophoretic separation of proteins, stained for protein.
Figure 5B:
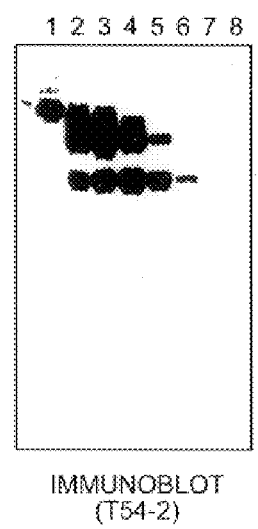
FIG. 5B is an immunoblot of separated proteins detected using the T54-2 antibody as a probe.
Figure 5C:
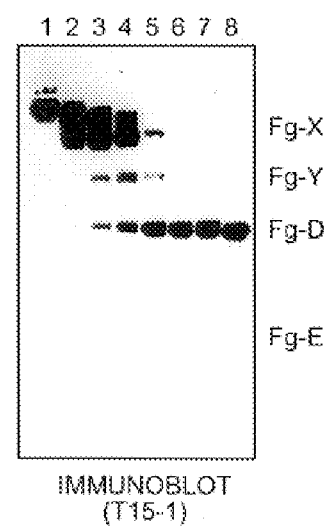
FIG. 5C is an immunoblot of separated proteins detected using the T15-1 antibody as the probe.

FIGS. 5A–5C show immunoblots of samples electrophoresed by SDS-PAGE, 5→15% gradient gels:

Lane 1: intact fibrinogen;
Lane 2: fibrinogen digested with plasmin for 60 min;
Lane 3: fibrinogen digested with plasmin for 90 min;
Lane 4: fibrinogen digested with plasmin for 120 min;
Lane 5: fibrinogen digested with plasmin for 180 min;
Lane 6: fibrinogen digested with plasmin for 240 min;
Lane 7: fibrinogen digested with plasmin for 360 min; and
Lane 8: fibrinogen digested with plasmin for 24 h.

Protein markers with indicated molecular weights (kDa) are shown in the extreme left lane of FIG. 5A. Digests were made in a buffer containing 10 mM $CaCl_2$, and were terminated at the specified time points by addition of aprotinin. FIG. 5A shows the protein-stained membrane, and FIGS. 5B and 5C show the antibody-reactive bands, using the T54-2 antibody according to the invention (FIG. 5B) and another MoAb T15-1 (FIG. 5C), detected using LUMI-NOL® as described above. Antibody T15-1 (IgG1, κ isotype) was derived from same fusion experiment that yielded T54-2. Like MoAb/T54-2, it reacts with Fg Bβ-chain/XL-Fb β-chain, but its epitope remains part of the terminal core Fragment D (Fg-D) no matter how long fibrinogen is digested with plasmin.

As shown in FIG. 5B, the epitope reactive with antibody T54-2 is present on fibrinogen and the transient fibrinogen degradation products called Fg-X ($M_r$~220–330 kDa) and Fg-Y ($M_r$~150–170 kDa), but is split from the terminal core fragment designated Fragment D (Fg-D, $M_r$~100 kDa).

FIG. 5C shows the reactivity of the samples with the MoAb designated T15-1 (IgG1, κ isotype), which reacts with Fg Bβ-chain/XL-Fb β-chain, but at an epitope that remains part of the terminal core Fragment D of fibrinogen digested with plasmin.

As will be shown below, the reactivity of T54-2 with non-reduced fibrinogen, Fg-X, Fg-Y illustrated by immunoblotting is most probably due to denaturation since, in solution, under "native" conditions, fibrinogen and these transient degradation products fail to react with T54-2, even at very high concentrations.

Figure 6A:
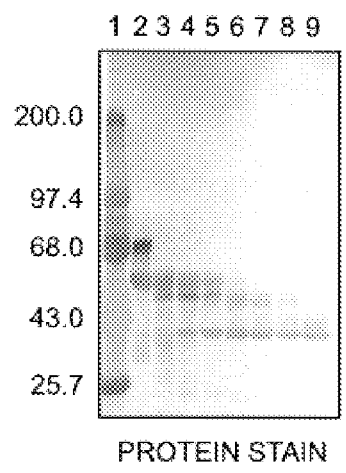
FIG. 6A is an electrophoretic separation of proteins, stained for protein.
Figure 6B:
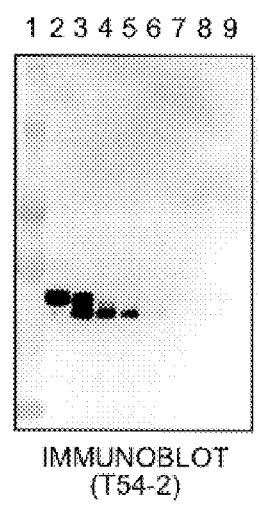
FIG. 6B is an immunoblot of separated proteins detected using the T54-2 antibody as a probe.
Figure 6C:
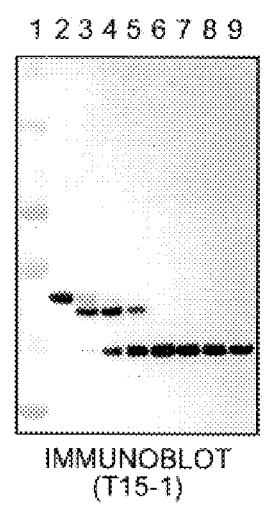
FIG. 6C is an immunoblot of separated proteins detected using the T15-1 antibody as a probe.

FIGS. 6A–6C show immunoblot results using the same samples separated in FIGS. 5A–5C, but following reduction with DTT. After exhaustive reduction with DTT, the samples were electrophoresed (SDS-PAGE, 5→15% gradient gels):

Lane 1: protein markers with indicated kDa;
Lane 2: fibrinogen;

Lane 3: fibrinogen digested with plasmin for 60 min;
Lane 4: fibrinogen digested with plasmin for 90 min;
Lane 5: fibrinogen digested with plasmin for 120 min;
Lane 6: fibrinogen digested with plasmin for 180 min;
Lane 7: fibrinogen digested with plasmin for 240 min;
Lane 8: fibrinogen digested with plasmin for 360 min; and
Lane 9: fibrinogen digested with plasmin for 24 h.

Antibody-bound protein bands were detected using RAM-HRPO, $H_2O_2$ and 4-chloro-1-naphthol. These results are in agreement with FIGS. 5A–5C, confirming that the β-chain (~40 kDa) of FgD is missing the epitope reactive with antibody T54-2. By the same token, it is clear that this same chain, obtained at different stages of digestion with plasmin, is fully reactive with antibody T15-1.

EXAMPLE 6

Characteristics of MoAb/T54-2 Reactive Peptide Present in a Trypsin Digest of Reduced/Alkylated Fibrinogen (SCM-Fg)

MoAb T54-2 also reacts with low molecular weight (<2 kDa) plasmin degradation product(s) of fibrinogen. We have also found that this antibody reacts with a peptide present in a trypsin digest of reduced/alkylated fibrinogen. To identify the structure of this peptide, a trypsin digest of SCM-Fg was separated by reverse phase high pressure liquid chromatography (HPLC, Vydac 214TP butyl $C_4$ column 10×250 mm) using standard methods. A fraction containing a mixture of peptides was found to be reactive with antibody T54-2. The HPLC fraction was subsequently further purified by size exclusion chromatography (SUPERDEX® Peptide HR 10/30 column 10×300–310 mm, Pharmacia Biotech).

Figure 7:
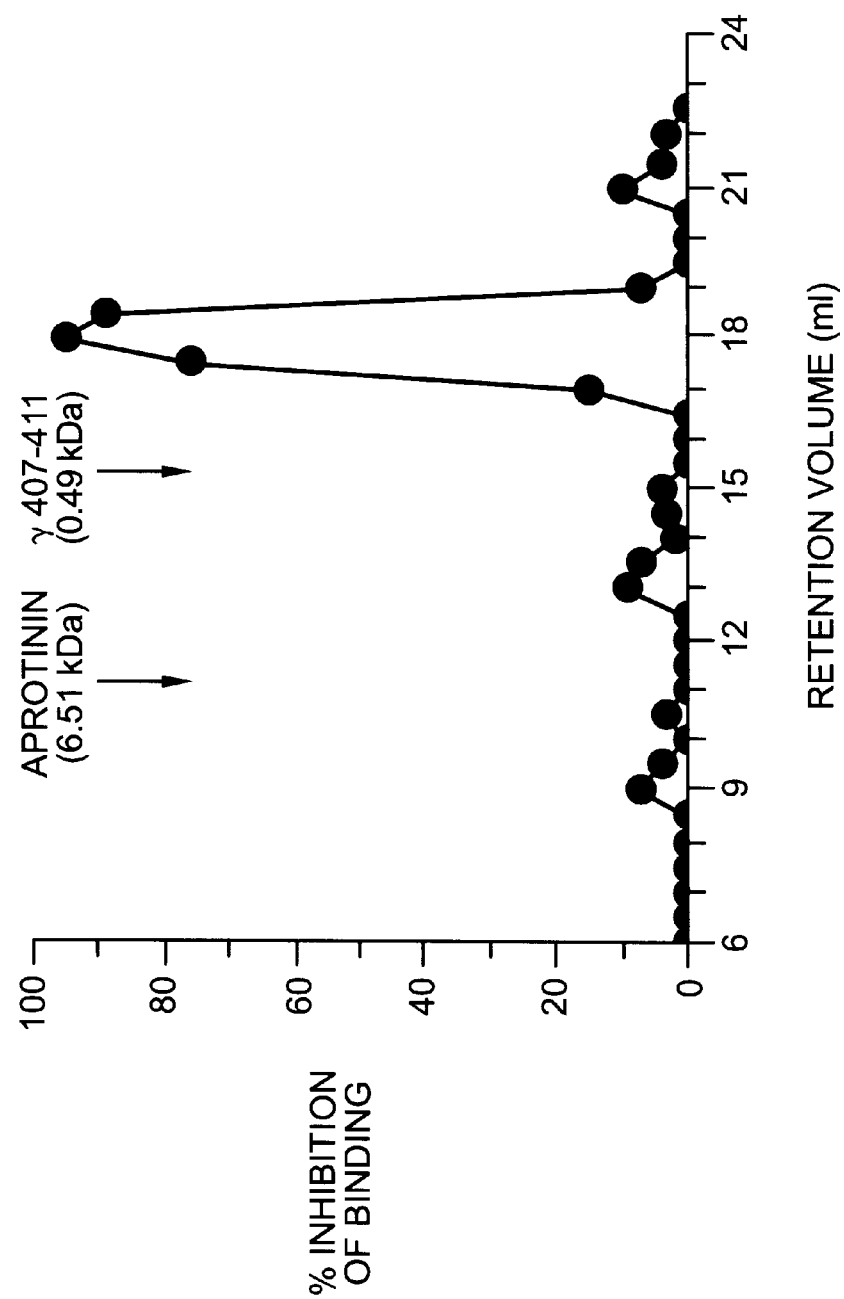
FIG. 7 is a graph illustrating a size exclusion separation of a small peptide fragment (largest peak) of fibrinogen that binds specifically with a monospecific antibody according to the invention. The inset of FIG. 7 is a graph illustrating a reverse phase HPLC separation of this fragment.

FIG. 7 shows the T54-2 immunoreactivity profile of fractions obtained by the second purification step. The principal graph in FIG. 7 shows that the major fraction reactive with T54-2 eluted with a retention volume of ~18 mL. The inset of FIG. 7 shows a single symmetrical peak ($R_t$ ~45.6 min) on reverse phase HPLC, which yielded an N-terminal sequence corresponding to Bβ123-127, i.e., the 5 mer DLWQK (SEQ ID NO:1) (Bini et al. 1996).

The calculated molecular weight of Bβ123-127 is ~0.69 kDa. At present we do not understand why this peptide has a retention volume on the SUPERDEX® Peptide HR 10/30 column that is greater than a somewhat smaller-size peptide derived from the C-terminal part of fibrinogen γ-chain (γ407–411, 0.49 kDa). The latter peptide and aprotinin (TRASYLOL®, 6.51 kDa) were used as markers for size exclusion chromatography (appearing as the smaller peaks in FIG. 7).

Figure 8:
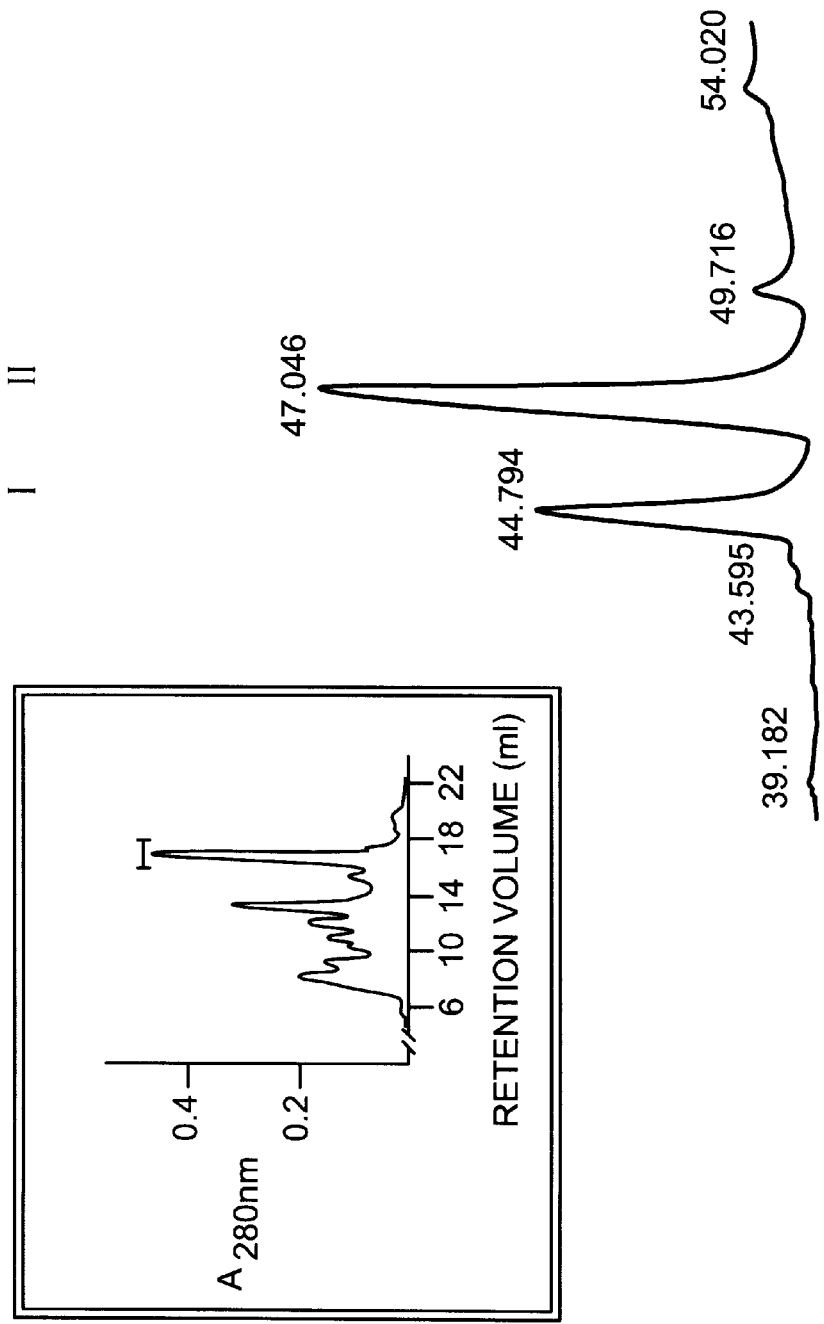
FIG. 8 is a reverse phase HPLC separation of plasmin-generated peptides that specifically bind with the T54-2 antibody according to the invention. The inset shows a size exclusion pattern of small peptides resulting from the plasmin digest of fibrinogen, with the indicated pooled fractions collected for HPLC fractionation.

We have now also shown that this peptide, and a related peptide (Bβ123-128, i.e., DLWQKR (SEQ ID NO:2)), can be isolated from late stage plasmin digests of fibrinogen. FIG. 8 is a graph illustrating reverse phase HPLC separation of plasmin-generated peptides that specifically bind with the T54-2 antibody according to the invention. The two major peaks (Peptide I [$R_t$=44.794 min] and II [$R_t$=47.046 min]) correspond to Bβ123-128 ("Peptide I") the smaller Bβ123-127 ("Peptide II") (sequencing data not shown). The inset of FIG. 8 shows the size exclusion pattern (by FPLC, see methods in Example 6) of small (<10 kDa) peptides found in a plasmin digest of fibrinogen. The fraction eluting with a retention volume of ~17–18 mL (pooled as indicated), and specifically binding with the T54-2 monospecific antibody of the invention, was selected for the HPLC fractionation.

The findings illustrated in FIG. 8 complement and explain the results presented in FIGS. 5A–5C and 6A–6C. That is, late stage plasmin digests (>4 h) result in removal of T54-2-reactive Bβ123-127 or peptides containing this segment of the Bβ-chain. Since these peptides are too small to be retained on the acrylamide gel, or are lost during transfer to nitrocellulose, late-stage plasmin digests do not show reactive bands by immunoblotting with T54-2.

EXAMPLE 7

Binding ELISA of T54-2 and other MoAbs with MMP-3 or Plasmin Digests of Fibrin(ogen)

Table 1 presents binding-ELISA results comparing the relative reactivities of a panel of monoclonal antibodies, including T54-2, with MMP-3 or plasmin digests of fibrin (ogen). The ELISAs were performed as follows: The indicated digests, diluted to ~10 μg/mL, were coated onto plastic plates. After overnight incubation, washing, and blocking, a specific antibody was added. Binding was determined by addition of RAM-HRPO, $H_2O_2$, and o-dianisidine. The color intensity (OD at 490 nm) for each antibody-"coated" digest combination is presented.

All but three antibodies tested in this experiment reacted with one of the fibrin(ogen) chains or chain segments. Antibodies Fd4-7B3, Fd4-4E1, and 2N3H10 reacted with intact fibrinogen or specified plasmin-derived core fragment of fibrin(ogen). In contrast to Fd4-7B3, antibody Fd4-4E1 reacted only with Fg-$D_1$ prepared in buffers containing $Ca^{2+}$.

We have previously shown that MMP-3 digests of XL-Fb do not react with antibody 4A5 (Bini et al. 1996). The low level of reactivity with this same digest and antibody 4-2 in binding ELISA (Table 1) is puzzling since, on immunoblotting, this same antibody reacts very well with such digests. However, it is clear that T54-2 reacts almost identically with MMP-3 digests of both Fg and XL-Fb but totally fails to react with plasmin digests of fibrinogen in buffers with or without $Ca^{2+}$. As described above, late stage plasmin digests of fibrinogen fail to react on immunoblotting because all reactivity with antibody T54-2 is present on a peptide(s) which is too small to be retained on the acrylamide gel or is lost during transfer to nitrocellulose. Similarly, the plasmin-generated peptide(s) is either too small to bind to ELISA plates or, if bound, can no longer react with antibody T54-2. Clearly, this is not the case with MMP-3 digests of either Fg or XL-Fb.

TABLE 1

Reactivity of MoAb/T54-2 and Other MoAbs with MMP-3 and Plasmin Digests of Fibrin)ogen

| Antibody | Antibody Specificity | Fibrinogen + MMP-3 | XL-Fb + MMP-3 | Fibrinogen + Plasmin (in EDTA buffer) | Fibrinogen + Plasmin (in $Ca^{2+}$ buffer) |
|---|---|---|---|---|---|
| 4-2 | γ 392-406 | 0.47 | 0.09 | 0.00 | 0.57 |
| 4A5 | γ 397-411 | 0.00 | 0.00 | 0.00 | 0.38 |

TABLE 1-continued

Reactivity of MoAb/T54-2 and Other MoAbs with MMP-3 and Plasmin Digests of Fibrin)ogen

| Antibody | Antibody Specificity | Fibrinogen + MMP-3 | XL-Fb + MMP-3 | Fibrinogen + Plasmin (in EDTA buffer) | Fibrinogen + Plasmin (in $Ca^{2+}$ buffer) |
|---|---|---|---|---|---|
| FD4-7B3 | Fg-$D_1$/Fg-$D_3$ | 0.59 | 0.21 | 0.23 | 0.53 |
| Fd4-4E1 | Fg-$D_1$ only | 0.83 | 0.28 | 0.00 | 0.59 |
| T54-2 | Bβ 123-127 | 0.75 | 0.58 | 0.00 | 0.00 |
| T56-5 | γ 95-265 | 0.02 | 0.00 | 0.01 | 0.02 |
| 1D4 | Aα 349-406 | 0.00 | 0.00 | 0.11 | 0.20 |
| 2N3H10 | Fg-E | 0.23 | 0.28 | 0.27 | 0.41 |
| Ea3 | Bβ 134-461 | 0.16 | 0.11 | 0.17 | 0.24 |
| T59-3 | γ 385-406 | 0.52 | 0.10 | 0.01 | 0.47 |
| 1C2-2 | Aα 529-539 | 0.03 | 0.00 | 0.06 | 0.05 |

EDTA: ethylenediaminetetraacetic acid
Fg-D1: C-terminal fragment (~93 kDa) of fibrinogen obtained by plasmin digestion in buffers containing $CaCl_2$
Fg-$D_3$: C-terminal fragment (~80 kDa) of fibrinogen obtained by plasmin digestion in buffers containing EDTA
Fg-E: N-terminal fragments (~50 kDa) obtained by plasmin digestion, the formula for the predominant species is given by (Aα 20–78, Bβ 54–122, γ 1–53)$_2$
Xl-Fb: Factor XIIIa cross-linked fibrin

EXAMPLE 8

Binding ELISA of T54-2 and other MoAbs with MMP-7 or Plasmin Digests of Fibrin(ogen)

Table 2 shows binding ELISA results using the same panel of antibodies under the same conditions described in Example 7, to examine reactivity with MMP-7 or plasmin digests of fibrin(ogen).

Unlike in MMP-3 digests of XL-Fb, the epitope reactive with antibody 4A5 is not destroyed by cleavage with MMP-7. As with MMP-3 digests, strong reactivity is observed between antibody T54-2 and MMP-7 digests of Fg and XL-Fb. No significant binding of T54-2 to plasmin digests is seen.

Figure 10A:
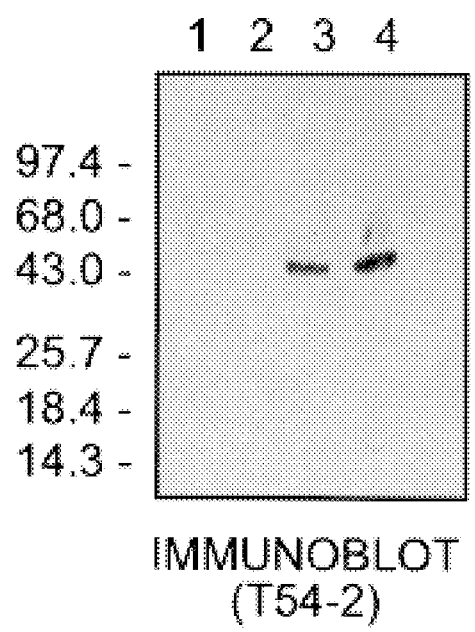
FIG. 10A is an immunoblot of separated proteins using the T54-2 antibody as a probe.
Figure 10B:
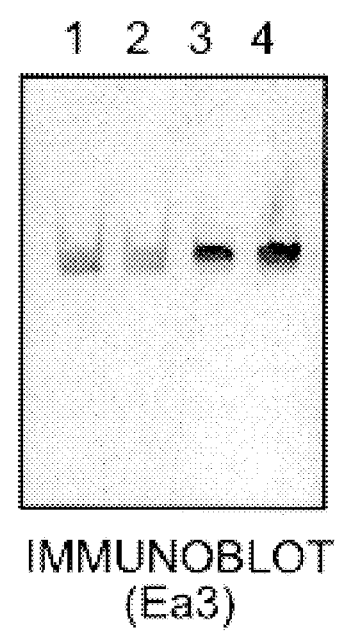
FIG. 10B is an immunoblot of separated proteins using the Ea3 antibody as a probe.

Specifically, FIGS. 9A and 9B show immunoblots of non-reduced samples, following electrophoresis (SDS-PAGE, 5% gels):
Lane 1: plasmin digest of Fg in $Ca^{2+}$-containing buffer;
Lane 2: MMP-3 digest of XL-Fb; and
Lane 3: MMP-3 digest of Fg.
Antibody-reactive bands were detected as described in Example 2.
FIGS. 10A and 10B show immunoblots of the same samples, except electrophoresed after exhaustive reduction with DTT (SDS-PAGE, 7% gels):
Lane 1: plasmin digest of Fg in $Ca^{2+}$-free buffer;
Lane 2: plasmin digest of Fg in $Ca^{2+}$-containing buffer ;
Lane 3: MMP-3 digest of XL-Fb; and
Lane 4: MMP-3 digest of Fg.

TABLE 2

Reactivity of MoAb/T54-2 and Other MoAbs with MMP-7 and Plasmin Digests of Fibrin(ogen)

| Antibody | Antibody Specificity | Fibrinogen + MMP-7 | XL-Fb + MMP-7 | Fibrinogen + Plasmin (in EDTA buffer) | Fibrinogen + Plasmin (in $Ca^{2+}$ buffer) |
|---|---|---|---|---|---|
| 4-2 | γ 392-406 | 0.77 | 0.94 | 0.45 | 1.24 |
| 4A5 | γ 397-411 | 7.51 | 7.49 | 0.00 | 1.29 |
| Fd4-7B3 | Fg-$D_1$/Fg-$D_3$ | 1.99 | 7.50 | 1.48 | 1.31 |
| Fd4-4E1 | Fg-$D_1$ only | 6.98 | 7.49 | 0.00 | 1.67 |
| T54-2 | Bβ 123-127 | 1.42 | 1.89 | 0.01 | 0.01 |
| T56-5 | γ 95-265 | 0.07 | 0.07 | 0.11 | 0.05 |
| 1D4 | Aα 349-406 | 0.89 | 1.61 | 1.18 | 1.27 |
| 2N3H10 | Fg-E | 2.22 | 7.49 | 1.28 | 1.16 |
| Ea3 | Bβ 134-461 | 0.74 | 0.51 | 0.79 | 0.95 |
| T59-3 | γ 385-406 | 0.34 | 0.24 | 0.34 | 1.13 |
| 1C2-2 | Aα 529-539 | 0.16 | 1.18 | 0.36 | 0.39 |

EXAMPLE 9

Immunoblot Analysis Using Plasmin or MMP-3 Digests and Antibodies T54-2 (anti-Bβ123-127), 4-2 (anti-γ392-406), and Ea3 (anti-Bβ134-461)

The binding ELISA results presented above suggested that some or all of the T54-2-reactive peptide (Bβ123-127) present in both MMP-3 and -7 digests is part of a larger degradation product which, when bound to ELISA plates, can efficiently interact with antibody T54-2. FIGS. 9A–9B and 10A–10B show immunoblots using antibody T54-2 (and others) as a probe of MMP-3 or plasmin digests, before (FIGS. 9A–9B) and after reduction with DTT (FIGS. 10A–10B).

Antibody-reactive bands were detected as described in Example 2. The epitope reactive with Ea3 has as yet to be precisely located but clearly it cannot be positioned at the N-terminal end (Bβ124-133) of the Bβ-chain of MMP-3-derived D/D-dimer fragments.

EXAMPLE 10

Immunoblot Analysis Using Plasmin or MMP-7 Digests and Antibodies T54-2 (anti-Bβ123-127) and Ea3 (anti-Bβ134-461)

Figure 11A:
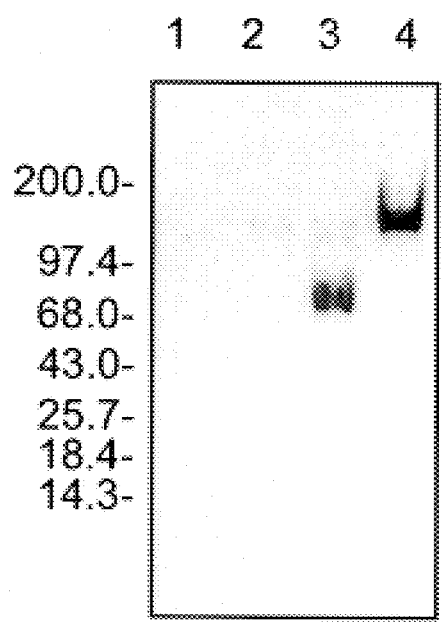
FIG. 11A is an immunoblot of separated proteins using the T54-2 antibody as a probe.
Figure 11B:
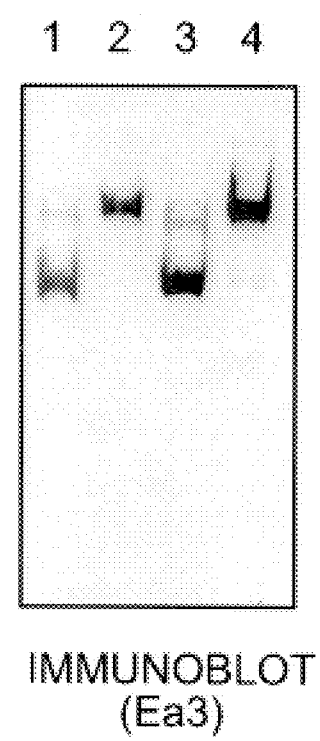
FIG. 11B is an immunoblot of separated proteins using the Ea3 antibody as a probe.

The following samples (non-reduced) were electrophoresed (SDS-PAGE, 5% gels). the separated samples were then probed using the antibodies T54-2 (anti-Bβ123-127) or Ea3 (anti-Bβ134-461). The results are shown in FIGS. 11A and 11B:

Lane 1: plasmin digest of Fg in $Ca^{2+}$-containing buffer;

Lane 2: plasmin digest of XL-Fb in $Ca^{2+}$-containing buffer;

Lane 3: MMP-7 digest of Fg; and

Lane 4: MMP-7 digest of XL-Fb.

Antibody-reactive bands were detected as described for the blots shown in FIGS. 3A–3C.

Figure 12A:
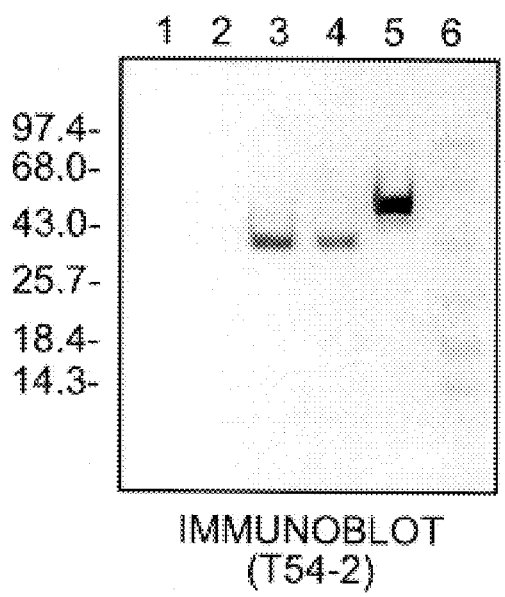
FIG. 12A is an immunoblot of separated proteins using the T54-2 antibody as a probe.
Figure 12B:
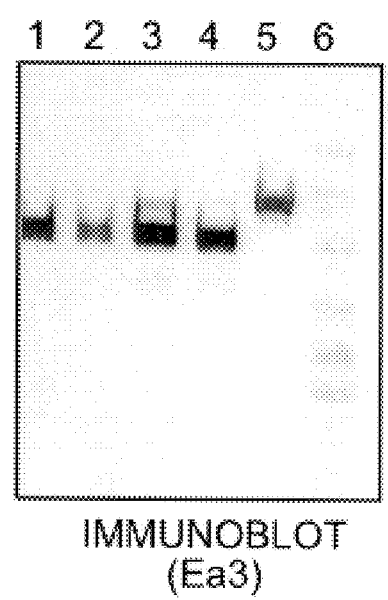
FIG. 12B is an immunoblot of separated proteins using the Ea3 antibody as a probe.

FIG. 12 is an immunoblot of samples corresponding to those identified in FIGS. 11A and 11B, after exhaustive reduction with DTT, and electrophoresis (SDS-PAGE, 7% gels):

Lane 1: plasmin digest of Fg in $Ca^{2+}$-containing buffer;

Lane 2: plasmin digest of XL-Fb in $Ca^{2+}$-containing buffer;

Lane 3: MMP-7 digest of Fg;

Lane 4: MMP-7 digest of XL-Fb;

Lane 5: non-digested fibrinogen;

Lane 6: protein markers with indicated kDa.

Antibody reactive bands were detected as described for the blots shown in FIGS. 3A–3C.

Fragment D-like (fastest moving bands) and larger core fragments present in MMP-3 digests (FIGS. 9A–9B, lanes 2 and 3) react similarly with antibodies 4-2 and T54-2. For reasons already explained above, the plasmin-generated Fragments D/D-dimer cannot bind antibody T54-2. Since the latter is directed to Bβ123-127 and since other groups have already shown that the N-terminal residue of the Bβ-chain of plasmin-generated Fragment D (or D-dimer) is Bβ Asp 134, the epitope reactive with this antibody cannot be part of either plasmin-generated core fragment. Clearly, MMP-3 cleavage must occur closer to the N-terminus of Fg Bβ-chain/XL-Fb β-chain. Since MMP-7 digests of Fg and XL-Fb also react with antibody T54-2 (see FIGS. 7 and 8), cleavage with this enzyme may be at/near the MMP-3 site. In fact, we have recently identified Bβ Leu124 as one of the N-terminal residues of D-dimer generated by MMP-7. It appears that at least these two MMPs cleave fibrin(ogen) Bβ/β-chain at the N-terminal side of the plasmin cleavage site located at Bβ Lys133-Asp134.

EXAMPLE 11

ELISA-Determined Standard Dose-Response Curves of Reactivity Between the Indicated Competitors and T54-2 (Anti-Bβ123-127)

Figure 13:
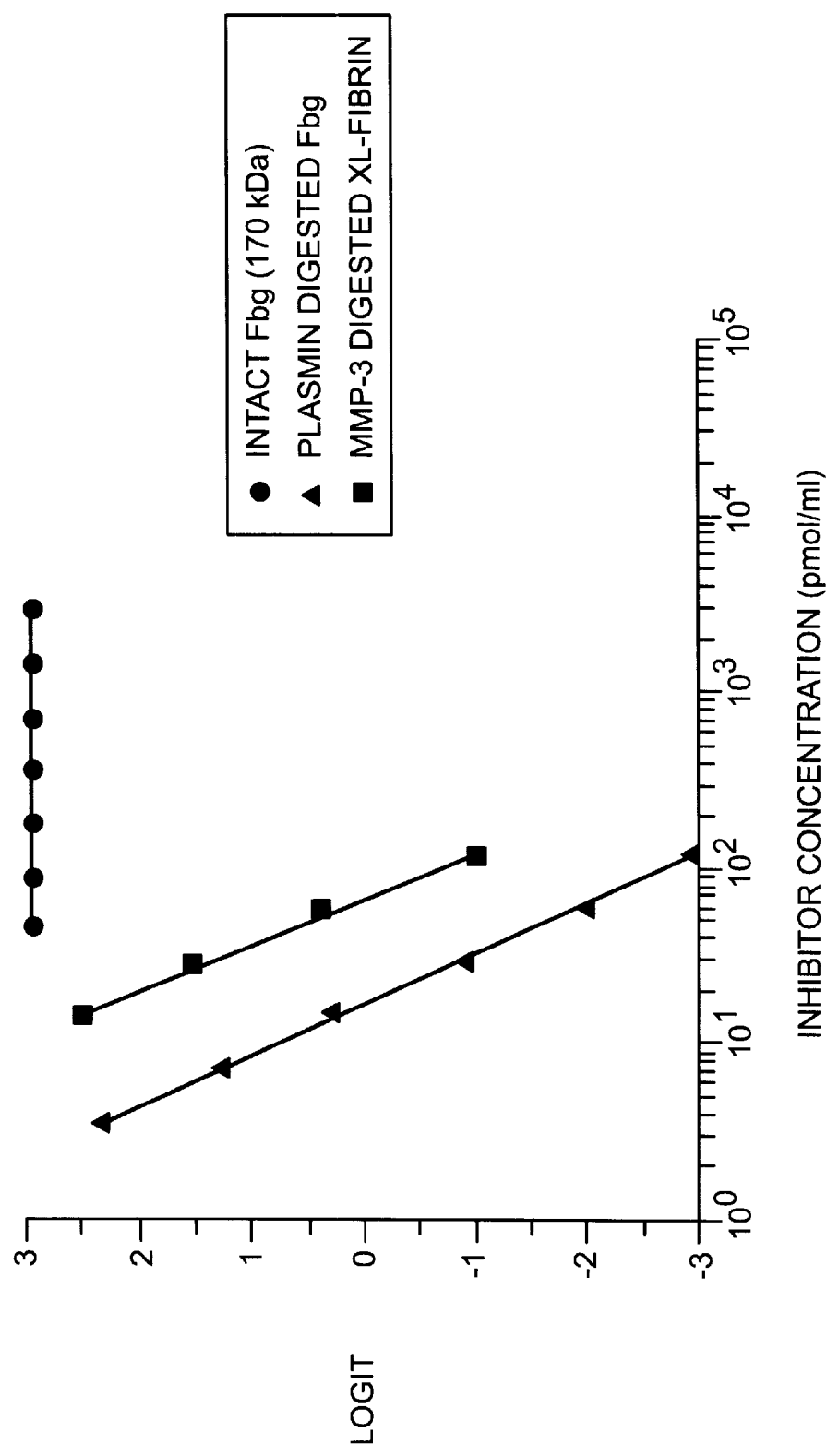
FIG. 13 is a graph illustrating a competition ELISA experiment, showing that a monospecific antibody of the invention binds to fragments of fibrinogen and cross-linked fibrin, but not to intact fibrinogen.

In these experiments, plates were coated with the β-chain (Bβ15-461) of fibrin. The results are shown in FIG. 13. The inhibition observed with the terminal (24 h) plasmin digest of fibrinogen (Fg) is due to peptide Bβ123-127. In contrast, the inhibition observed with the MMP-3 digested XL-Fb is due to some or all of the large-sized core fragments which immunoblot with this same antibody (see FIGS. 9A–9B, lane 2). Inhibition was determined as follows: $(A/A_o) \times 100$ where A is absorbance in presence of competitor and $A_o$ is absorbance in control wells (buffer with no competitor added). Response data were linearized by means of logit transforms (Rodbard et al. 1969).

Since markers reactive with MoAbs 4A5, 1D4, and T54-2 are either lost or are generated in the course of digestion with MMPs, immunoassays with these antibodies can be used in determining digestion rates with each enzyme, under different experimental conditions. The antibodies, alone or in combinations, can also be helpful in identifying the enzyme or enzymes responsible for proteolysis, e.g., as an index of in vivo proteolysis. MMP-3-derived D/D-dimer Fragments react ($IC_{50}$ ~70 pmol/mL) with antibody T54-2 but those generated by plasmin do not (FIG. 13). The inhibition observed with the terminal plasmin Fg digest (24 h) is due to peptide Bβ123-127. In contrast, the inhibition observed with the MMP-3 digested XL-Fb (FIG. 13) is due to some or all of the large-sized core fragments which immunoblot with this same antibody (see FIGS. 9A–9B, lane 2). Most importantly, since intact Fg fails to react with this antibody (FIG. 13), patient plasma reactive with T54-2 may be indicative of in vivo MMP-3 activity.

The use of MoAb/T54-2 and other monospecific antibodies in immunometric assays, such as RIA, ELISA, immunoblot analysis, and the like, can be used in determining in vivo activity of fibrinolytic MMPs, including MMP-3, -7 and other, yet to be tested MMPs. Since "non-denatured" plasma fibrinogen is totally unreactive with antibody T54-2, any reactivity (e.g., in RIA or ELISA) with plasma but not its ultrafiltrate, would be strongly indicative of presence of in vivo MMP-3 or MMP-7 activity.

As shown in FIGS. 9–12, immunoblot analysis (before/after reduction) using T54-2 and a suitable control antibody (Ea3 or T15-1, etc.) can be used to confirm the presence of Fragments D/D-dimer generated by MMP-3, MMP-7 or other fibrinolytic MMPs. MoAb/T54-2 will also find utility in immunohistochemical detection of MMP-3, MMP-7 or other MMP degraded fibrin(ogen)-related antigen in vascular and extravascular spaces.

BIOLOGICAL DEPOSIT

The hybridoma cell line T54-2, described herein above, was deposited under the provisions of the Budapest Treaty with the American Type Culture Collection, Manassas, Va., on Sep. 10, 1997 as ATCC Accession No. HB-12399. This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications have been mentioned in the foregoing specification, and are incorporated herein by reference for all that they disclose:

Bilezikian S B and Nossel H L, "Unique pattern of fibrinogen cleavage by human leukocyte proteases," *Blood* 50(1):21–28 (1977).

Bini A, Fenoglio J J, Sobel J, Owen J, Fejgl M, and Kaplan K L, "Immunochemical characterization of fibrinogen, fibrin I, and fibrin II in human thrombi and atherosclerotic lesions," *Blood* 69:1038–1045 (1987).

Bini A and Kudryk B J, "Fibrin and its derivatives in the normal and diseased vessel wall," *Ann NY Acad Sci* 667:112–126 (1992).

Bini A, Callender S, Procyk R, Blombäck B, and Kudryk B J, "Flow and antibody binding properties of hydrated fibrins prepared from plasma, platelet rich plasma and whole blood," *Thrombosis Res* 76:145–56 (1994).

Bini A., Itoh Y., Kudryk B J, Nagase H, "Degradation of cross-linked fibrin by matrix metalloproteinase 3 (stromelysin 1): Hydrolysis of the gamma Gly 404-Ala 405 peptide bond," *Biochemistry* 35(40):13056–13063 (1996).

Blombäck B, Blombäck M, Henschen A, Hessel B, Iwanaga S, and Woods K R, "N-terminal disulphide knot of human fibrinogen," *Nature* 218:130–134 (1968).

Blombäck B and Okada M, "Fibrin gel structure and clotting time," *Thromb Res* 25:51–70 (1982).

Blombäck B, Carlsson K, Fatah K, Hessel B, and Procyk R, "Fibrin in human plasma gel architectures governed by rate and nature of fibrinogen activation," *Thromb Res* 75:521–538 (1994).

Blombäck B, "Fibrinogen and fibrin formation and its role in fibrinolysis," in Goldstein J, ed., *Biotechnology of Blood*, 225–279 (1991).

Budzynski A Z, "Interaction of hementin with fibrinogen and fibrin," *Blood Coagulation and Fibrinolysis* 2:149–52 (1991).

Campbell, "Monoclonal antibody technology, the production and characterization of rodent and human hybridomas" in Burdon et al., eds, *Laboratory Techniques in Biochemistry and Molecular Biology*, Volume 13, Elsevier Science Publishers, Amsterdam (1985).

Chen R and Doolittle R F, "Cross-linking sites in human and bovine fibrin," *Biochemistry* 10:4487–4491 (1971).

Cheresh D A, Berliner S A, Vicente V, and Ruggeri Z M, "Recognition of distinct adhesive sites on fibrinogen by related integrins on platelets and endothelial cells," *Cell* 58:945–953 (1989).

Chung D W, Harris J E, and Davie E W, "Nucleotide sequences of the three genes coding for human fibrinogen," *Adv Exp Med Biol* 281:39–48 (1991).

Collen D, Kudryk B, Hessel B, and Blombäck B, "Primary structure of human fibrinogen and fibrin. Isolation and partial characterization of chains of fragment D," *J Biol Chem* 250(15):5808–5817 (1975).

Collen D, "On the regulation and control of fibrinolysis," *Thromb Haemost* 43:77–89 (1980).

Collen D and Lijnen H R, "Basic and clinical aspects of fibrinolysis and thrombolysis," *Blood* 78(12):3114–3124 (1991).

Deutsch D G and Mertz E T, "Plasminogen: Purification from human plasma by affinity chromatography," *Science* 170:1095–1096 (1970).

Doolittle R F, Watt K W K, Cottrell B A, Strong D D, and Riley M, "The amino acid sequence of the alpha-chain of human fibrinogen," *Nature* 280:464–468 (1979).

Doolittle R F, "Fibrinogen and fibrin," *Annu Rev Biochem* 53:195–229 (1984).

Doolittle R F, "Fibrinogen and fibrin," in Bloom A L, and Thomas D P, eds., *Hemostasis and Thrombosis* Churchill Livingston, Edinburgh, N.Y. (1987).

Dvorak H F, Nagy J A, Berse B, Brown L F, Yeo K-T, Yeo T-K, Dvorak A M, Van de Water L, Sioussat T M, and Senger D R, "Vascular Permeability factor, fibrin, and the pathogenesis of tumor stroma formation," *Ann NY Acad Sci* 667:101–111 (1992).

Engvall E and Ruoslahti E, "Binding of soluble form of fibroblast surface protein, fibronectin, to collagen," *Int J Cancer* 20(1):1–5 (1977).

Ernst E, "Plasma fibrinogen—An independent cardiovascular risk factor," *J Internal Med* 227:365–372 (1990).

Ernst E and Resch K L, "Fibrinogen as a cardiovascular risk factor: A meta-analysis and review of the literature," *Ann Intern Med* 118:956–963 (1993).

Farrell D H, Thiagarajan P, Chung D W, and Davie E W, "Role of fibrinogen alpha and gamma chain sites in platelet aggregation," *Proc Natl Acad Sci USA* 89:10729–10732 (1992).

Felding-Habermann B, Ruggeri Z M, and Cheresh D A, "Distinct biological consequences of integrin alpha-v-beta-3-mediated melanoma cell adhesion to fibrinogen and its plasmic fragments," *J Biol Chem* 267:5070–5077 (1992).

Francis C W and Marder V J, "Physiologic regulation and pathologic disorders of fibrinolysis," Chapter 54 in *Hemostasis and Thrombosis: Basic Principles and Clinical Practice*, 3rd ed., Colman R W, Hirsh J, Marder V J, and Salzman E W, eds., J B Lippincott Co, Philadelphia (1994).

Fu Y, Weissbach L, Plant P W, Oddoux C, Cao Y, Liang T J, Roy S N, Redman C M, and Grieninger G, "Carboxy-terminal-extended variant of the human fibrinogen α subunit: A novel exon conferring marked homology to β and γ subunits," *Biochemistry* 31:11968–11972 (1992).

Fu Y and Grieninger G, "Fib$_{420}$: A normal human variant of fibrinogen with two extended α chains," *Proc Natl Acad Sci USA* 91:2625–28 (1994).

Gabriel D A, Muga K, and Boothroyd E M, "The effect of fibrin structure on fibrinolysis," *J Biol Chem* 267:24259–63 (1992).

Goding J W, in *Monoclonal Antibodies: Principles and Practice*, Academic Press, New York, N.Y. (1986).

Gonda S R and Shainoff J R, "Adsorptive endocytosis of fibrin monomer by macrophages: Evidence of a receptor for the amino terminus of the fibrin alpha chain," *Proc Natl Acad Sci USA* 79:4565–4569 (1982).

Gramse M, Bingenheimer C, and Schmidt W, "Degradation products of fibrinogen by elastase-like neutral protease from human granulocytes. Characterization and effects on blood coagulation in vitro," *J Clin Invest* 61(4):1027–1033 (1978).

Guan A L, D Retzios, G N Henderson, and F S Markland, "Purification and characterization of a fibrinolytic enzyme from venom of the southern copperhead snake (*Agkistrodon contortrix contortrix*)," *Arch Biochem Biophys* 289(2):197–207 (1991).

Harlow E and Lane D, *Antibodies: A Laboratory Manual*, Cold Spring Harbor Laboratory Press, Cold Spring Harbor, N.Y. (1988).

Henschen A and Lottspeich F, "Amino Acid sequence of human fibrin, preliminary note on the completion of the beta-chain sequence," *Hoppe-Seyler's Z Physiol Chem* 358:1643–1646 (1977).

Henschen A, Lottspeich F, and Hessel B, "Amino acid sequence of human fibrin, preliminary note on the completion of the intermediate part of the alpha-chain sequence," *Hoppe-Seyler's Z Physiol Chem* 360:1951–1956 (1979).

Huse W D, Sastry L, Iverson S A, Kang A S, Alting-Mees M, Burton D R, Benkovic S J, and Lerner R A, "Generation of a large combinatorial library of the immunoglobulin repertoire in phage lambda," *Science* 246:1275–1281 (1989).

Hynes R O, "Integrins: Versatility, modulation, and signaling in cell adhesion," *Cell* 69:11–25 (1992).

Kant J A, Fornace Jr A J, Saxe D, Simon M I, McBride O W, and Crabtree G R, "Evolution and organization of the fibrinogen locus on chromosome 4: Gene duplication accompanied by transposition and inversion," *Proc Natl Acad Sci USA* 82:2344–2348 (1985).

Kennett R H, McKearn T J, and Bechtol K B, eds., *Monoclonal Antibodies Hybridomas: A New Dimension in Biological Analyses*, Plenum Press, New York (1980).

Kloczewiak M, Timmons S, Lukas T J, and Hawiger J, "Platelet receptor recognition site on human fibrinogen Synthesis and structure-function relationship of peptides corresponding to the carboxy-terminal segment of the gamma chain," *Biochemistry* 23:1767–1774 (1984).

Köhler G and Milstein C, "Continuous cultures of fused cells secreting antibody of predefined specificity," *Nature* 256:495–497 (1975).

Kudryk B, Rohoza A, Ahadi M, Chin J, and Wiebe M E, "A monoclonal antibody with ability to distinguish between $NH_2$-terminal fragments derived from fibrinogen and fibrin," *Molec Immun* 20:1191–1200 (1983).

Kudryk B, Rohoza A, Ahadi M, Chin J, and Wiebe M E, "Specificity of a monoclonal antibody for the $NH_2$-terminal region of fibrin," *Mol Immunol* 21:89–94 (1984).

Kudryk B J, Grossman Z D, McAfee J G, and Rosebrough S F, "Monoclonal antibodies as probes for fibrin(ogen) proteolysis," C.hapter 19 in *Monoclonal Antibodies in Immunoscintigraphy*, Chatal J-F, ed., CRC Press, Boca Raton (1989a).

Kudryk B, Gidlund M, Rohoza A, Ahadi M, Coiffe D, and Weitz J I, "Use of a synthetic homologue of human fibrinopeptide A for production of a monoclonal antibody for the free peptide," *Blood* 74(3):1036–1044 (1989b).

Kudryk B, Rohoza A, Ahadi M, Gidlund M, Procyk R, and Matsueda G R, *Thromb Haemostas* 65:898 (Abstract 714) (1991).

Kudryk B, Bini A, Procyk R, Matsueda G R, and Shainoff J R, "Cross-linking of fibrinogen by tissue transglutaminase: Involvement of the C-termini of the Aα- and γ-chains in formation of Aαγ-dyads," *Thromb Haemostas* 69(6):1260 (1993)

Laemmli U K, "Cleavage of structural proteins during the assembly of the head of bacteriophage T4," *Nature* 227:680–685 (1970).

Laemmli U K, and M Favre, "Maturation of the head of bacteriophage T4. I. DNA packaging events," *J Mol Biol* 80:575–99 (1973).

Lamoyi E and Nisonoff A, "Preparation of F(ab')$_2$ fragments from mouse IgG of various subclasses," *J Immunol Meth* 56:235–243 (1983).

Liu C Y, Sobel J H, Weitz J I, Kaplan K L, and Nossel H L, "Immunologic identification of the cleavage products from the A alpha- and B beta-chains in the early stages of plasmin digestion of fibrinogen," *Thromb Haemostas* 56(1):100–106 (1986).

Loewy A G, Santer U V, Wieczorek M, Blodgett J K, Jones S W, and Cheronis J C, "Purification and characterization of a novel zinc-proteinase from cultures of *Aeromonas hydrophila*," *J Biol Chem* 268:9071–78 (1993).

Loike JD, Sodeik B, Cao L, Leucona S, Weitz J I, Detmers P A, Wright S D, and Silverstein S C, "CD11c/CD18 on neutrophils recognizes a domain at the N terminus of the A-alpha chain of fibrinogen," *Proc Natl Acad Sci USA* 88:1044–1048 (1991).

Lottspeich F and Henschen A, "Amino acid sequence of human fibrin Preliminary note on the completion of the gamma-chain sequence," *Hoppe-Seyler's Z Physiol Chem* 358:935–938 (1977).

Matrisian L M, "The matrix-degrading metalloproteinases," *BioEssays* 14:455–63 (1992).

Matsudaira P, "Sequence from picomole quantities of proteins electroblotted onto polyvinylidene difluoride membranes," *J Biol Chem* 262(21):10035–10038 (1987).

Matsueda G R and Bernatowicz M S, pp 133–136 in *Fibrinogen 3—Biochemistry, Biological Functions, Gene Regulation and Expression* (Mosesson M W, Amrani D, Siebenlist K R, DiOrio R, eds) Elsevier *Science Publishers BV, Amsterdam* (1988).

McDonagh J, Messel H, McDonagh Jr R P, Murano G, and Blombäck B, "Molecular weight analysis of fibrinogen and fibrin chains by an improved sodium dodecyl sulfate gel electrophoresis method," *Biochim Biophys Acta* 257:135–42 (1972).

Murphy G, Atkinson S, Ward R, Gavrilovic J, and Reynolds J J, "The role of plasminogen activators in the regulation of connective tissue metalloproteinases," *Ann NY Acad Sci* 667:1–12 (1992).

Nagase H, Ogota Y, Suzuki K, Enghild J J, and Salvesen G, "Substrate specificities and activation mechanisms of matrix metalloproteinases," *Biochem Soc Trans* 19:715–18 (1991).

Okada Y, Nagase H, and Harris Jr ED, "A metalloproteinase from human rheumatoid synovial fibroblasts that digests connective tissue matrix components," *J Biol Chem* 261:14245–55 (1986).

Okada Y, Morodomi T, Enghild J J, Suzuki K, Yasui A, Nakanishi I, Salvesen G, and Nagase H, "Matrix metalloproteinase 2 from human rheumatoid synovial fibroblasts. Purification and activation of the precursor and enzymic properties," *Eur J Biochem* 194(3):721–730 (1990).

Parham P, "On the fragmentation of monoclonal IgG1, IgG2a, and IgG2b from BALB/c mice," *J Immunol* 131:2895–2902 (1983).

Plow E F and Edgington TS, "An alternative pathway for fibrinolysis. I. The cleavage of fibrinogen by leukocyte proteases at physiologic pH," *J Clin Invest* 56:30–38 (1975).

Plow E F, "The major fibrinolytic proteases of human leukocytes," *Biochim Biophys Acta* 630(1):47–56 (1980).

Plow E F and Edgington T S, "Surface markers of fibrinogen and its physiologic derivatives revealed by antibody probes," *Semin Thromb Haemostas* 8(1):36–56 (1982).

Procyk R, Adamson L, Block M, and Blombäck B, "Factor XIII catalyzed formation of fibrinogen-fibronectin oligomers—a thiol enhanced process," *Thromb Res* 40(6):833–852 (1985).

Procyk R, Kudryk B, Callender S, Blombäck B, "Accessibility of epitopes on fibrin clots and fibrinogen gels," *Blood* 77:1469–1475 (1991).

Purves L, Purves M, and Brandt W, "Cleavage of fibrin-derived D-dimer into monomers by endopeptidase from puff adder venom (*Bitis arietans*) acting at cross-linked sites of the γ-chain Sequence of carboxy-terminal cyanogen bromide γ-chain fragments," *Biochemistry* 26:4640–46 (1987).

Retzios A D and Markland Jr F S, "Purification, characterization, and fibrinogen cleavage sites of three fibrinolytic enzymes from the venom of *Crotalus basiliscus* basiliscus," *Biochemistry* 31:4547–57 (1992).

Ribes J A, Ni F, Wagner D D, and Francis C W, "Mediation of fibrin-induced release of von Willebrand factor from cultured endothelial cells by the fibrin beta chain," *J Clin Invest* 84:435–442 (1989).

Rodbard D, Bridson W, and Rayford P L, "Rapid calculation of radioimmunoassay results," *J Lab & Clin Med* 74(5):770–781 (1969).

Rotman, *Proc Natl Acad Sci USA* 47:1981–1991 (1961).

Sanchez E F, Magalhes A, Mandelbaum F R, and Diniz C R, "Purification and characterization of the hemorrhagic factor II from the venom of the Bushmaster snake (Lachesis muta muta)," *Biochim Biophys Acta* 1074:347–56 (1991).

Sehgal P B, Grieninger G, and Tosato G, eds., "Regulation of the acute phase and immune responses: Interleukin-6," *Ann NY Acad Sci* 557:1–583 (1989).

Senior R M, Griffin G L, Fliszar J, Shapiro S D, Goldberg G I, and Welgus H G, "Human 92- and 72-kilodalton type IV collagenases are elastases," *J Biol Chem* 266(12):7870–7875 (1991).

Siebenlist K R and Mosesson M W, "Factors affecting gamma-chain multimer formation in cross-linked fibrin," *Biochemistry* 31 (3):936–941 (1992).

Sterrenberg L, Gravesen M, Haverkate F, and Nieuwenhuizen W, "Granulocyte enzyme mediated degradation of human fibrinogen in plasma in vitro," *Thromb Res* 31(5):719–728 (1983).

Towbin H, Staehelin T, and Gordon J, "Electrophoretic transfer of proteins from polyacrylamide gels to nitrocellulose sheets: Procedure and some applications," *Proc Natl Acad Sci USA* 76(9):4350–4354 (1979).

Valenzuela R, Shainoff J R, DiBello P M, Urbanic D A, Anderson J M, Matsueda G R, and Kudryk B J, "Immunoelectrophoretic and immunohistochemical characterizations of fibrinogen derivatives in atherosclerotic aortic intimas and vascular prosthesis pseudo-intimas," *Amer J Pathol* 141:861–880 (1992).

Welgus H G, Campbell E J, Cury J D, Eisen A Z, Senior R M, Wilhelm S M, and Goldberg G I, "Neutral metalloproteinases produced by human mononuclear phagocytes. Enzyme profile, regulation, and expression during cellular development," *J Clin Invest* 86(5):1496–1502 (1990).

Werb Z, Alexander C M, and Adler R R, "Expression and function of matrix metalloproteinases in development," *Matrix Suppl* 1:337–343 (1992).

Woessner J F Jr, "Matrix metalloproteinases and their inhibitors in connective tissue remodeling," *FASEB J* 5(8):2145–2154 (1991).

Zavalova L L, Kuzina E V, Levina N B, and Baskova I P, "Monomerization of fragment DD by destabilase from the medicinal leech does not alter the N-terminal sequence of the γ-chain," *Thrombosis Res* 71:241–44 (1993).

---

---

What is claimed is:

1. A monospecific antibody, that binds specifically with an epitope consisting of an amino acid sequence SEQ ID NO: 1.

2. The monospecific antibody according to claim 1, wherein the antibody is detectably labeled by conjugation to a detectable moiety.

3. The monospecific antibody according to claim 2, wherein the detectable moiety is selected from the group consisting of radionuclides, enzymes, specific binding pair components, colloidal dye substances, fluorochromes, reducing substances, latexes, digoxigenin, metals, particulates, dansyl lysine, antibodies, protein A, protein G, electron dense materials, and chromophores.

4. The monospecific antibody according to claim 1, wherein the antibody is attached to a substrate.

5. The monospecific antibody according to claim 4, wherein the substrate includes a component selected from the group consisting of gels, hydrogels, resins, beads, nitrocellulose, nylon filters, microtiter plates, culture flasks, and polymeric materials.

6. The monospecific antibody according to claim 1, wherein the antibody is an antigen-binding fragment selected from the group consisting of Fab, F(ab')$_2$, and Fv fragments.

7. The monospecific antibody according to claim 1, wherein the antibody is a modified, synthetic, recombinant, or chimeric antibody.

8. The monospecific antibody according to claim 1, wherein the antibody is a monoclonal antibody.

9. The monoclonal antibody according to claim 8, wherein the antibody has all identifying characteristics of antibody produced by hybridoma cell line T54-2 deposited as ATCC Accession No. HB-12399.

10. The monoclonal antibody according to claim 9, wherein the antibody is produced by the hybridoma cell line T54-2.

11. A continuous cell line, that produces a monoclonal antibody that binds specifically with an epitope consisting of an amino acid sequence SEQ ID NO:1.

12. The continuous cell line according to claim 11, wherein the continuous cell line has all identifying characteristics of hybridoma cell line T54-2 deposited as ATCC Accession No. HB-12399.

13. The continuous cell line according to claim 12, wherein the cell line is the hybridoma cell line T54-2.

* * * * *